United States Patent
Jakel et al.

(10) Patent No.: US 11,519,013 B2
(45) Date of Patent: Dec. 6, 2022

(54) SYSTEM AND METHOD FOR PRODUCING A SUGAR STREAM WITH FRONT END OIL SEPARATION

(71) Applicant: Fluid Quip Technologies, LLC, Springfield, OH (US)

(72) Inventors: Neal Jakel, Cedar Rapids, IA (US); Albert Pollmeier, Cedar Rapids, IA (US)

(73) Assignee: Fluid Quip Technologies, LLC, Springfield, OH (US)

( * ) Notice: Subject to any disclaimer, the term of this patent is extended or adjusted under 35 U.S.C. 154(b) by 0 days.

(21) Appl. No.: 15/921,783

(22) Filed: Mar. 15, 2018

(65) Prior Publication Data

US 2019/0284593 A1  Sep. 19, 2019

(51) Int. Cl.
*C12P 19/02* (2006.01)
*C08L 3/02* (2006.01)
(Continued)

(52) U.S. Cl.
CPC .............. *C12P 19/02* (2013.01); *A23L 7/104* (2016.08); *A23L 29/35* (2016.08); *C08L 3/02* (2013.01);
(Continued)

(58) Field of Classification Search
CPC ........ C12P 19/02; C12C 11/075; C12C 5/004; C08L 3/02; B01D 37/00; B01D 2257/70;
(Continued)

(56) References Cited

U.S. PATENT DOCUMENTS 3,249,512 A * 5/1966 Bode ...................... C12P 19/20
426/10
4,330,625 A    5/1982 Miller et al.
(Continued)

FOREIGN PATENT DOCUMENTS

EP     3121258 A1    1/2017
WO  2012075481 A1    6/2012
(Continued)

OTHER PUBLICATIONS

European Patent Office, Extended Search Report issued in EP 19161947.7 dated Jul. 26, 2019, 9 pages.

*Primary Examiner* — Hamid R Badr
(74) *Attorney, Agent, or Firm* — Wood Herron & Evans LLP

(57) ABSTRACT

An improved dry grind system and method for producing a sugar stream from grains or similar carbohydrate sources and/or residues, such as for biochemical production, with front end oil separation. Prior to or after saccharification, oil can be removed from a sugar/carbohydrate stream. After saccharification and prior to a sugar conversion process, the sugar/carbohydrate stream includes a desired Dextrose Equivalent (DE) where DE describes the degree of conversion of starch to dextrose can be produced, with such sugar stream being available for biochemical production, e.g., alcohol production, or other processes. In addition, the systems and methods also can involve the removal of certain grain components, e.g., corn kernel components, including protein and/or fiber. In other words, oil separation and sugar stream production occurs on the front end of the system and method.

16 Claims, 6 Drawing Sheets

(51) Int. Cl.
  *C11C 1/10* (2006.01)
  *C12C 5/00* (2006.01)
  *C12C 11/07* (2006.01)
  *C12M 1/00* (2006.01)
  *A23L 7/104* (2016.01)
  *C12P 19/14* (2006.01)
  *C13K 1/06* (2006.01)
  *A23L 29/30* (2016.01)
  *B01D 3/14* (2006.01)
  *B01D 37/00* (2006.01)

(52) U.S. Cl.
  CPC ............... *C11C 1/10* (2013.01); *C12C 5/004* (2013.01); *C12C 11/075* (2013.01); *C12M 1/00* (2013.01); *C12M 21/00* (2013.01); *C12P 19/14* (2013.01); *C13K 1/06* (2013.01); *B01D 3/14* (2013.01); *B01D 37/00* (2013.01); *B01D 2257/70* (2013.01)

(58) Field of Classification Search
  CPC ............ C11C 1/10; A23L 7/104; A23L 29/35; C12M 1/00
  USPC .......................................................... 426/11
  See application file for complete search history.

(56) References Cited

U.S. PATENT DOCUMENTS

| | | | |
|---|---|---|---|
| 4,361,651 A | 11/1982 | Keim | |
| 4,407,955 A | 10/1983 | Muller et al. | |
| 4,448,790 A | 5/1984 | Sarkki et al. | |
| 4,448,881 A | 5/1984 | Muller et al. | |
| 4,578,353 A | 3/1986 | Assarsson et al. | |
| 5,559,031 A | 9/1996 | Zinnamosca et al. | |
| 6,962,722 B2 | 11/2005 | Dawley et al. | |
| 7,452,425 B1 | 11/2008 | Langhauser | |
| 7,481,890 B2 | 1/2009 | Cheryan | |
| 7,488,390 B2 | 2/2009 | Langhauser | |
| 7,494,675 B2 | 2/2009 | Abbas et al. | |
| 7,632,094 B2 | 12/2009 | Bruckmayer | |
| 7,985,847 B2 | 7/2011 | Belanger et al. | |
| 7,998,511 B2 | 8/2011 | Abbas et al. | |
| 8,278,080 B2 | 10/2012 | Yoon | |
| 8,293,504 B2 | 10/2012 | Boy et al. | |
| 8,557,540 B2 | 10/2013 | Burlew et al. | |
| 8,652,818 B2 | 2/2014 | Lawton, Jr. et al. | |
| 8,722,372 B2 | 5/2014 | Kiuchi et al. | |
| 8,778,433 B2 | 7/2014 | Lee | |
| 8,927,235 B2 | 1/2015 | Iyer et al. | |
| 9,012,191 B2 | 4/2015 | Lee | |
| 9,068,205 B2 | 6/2015 | Purtle et al. | |
| 9,273,329 B2 | 3/2016 | Kusuda et al. | |
| 9,523,104 B2 | 12/2016 | Fuchs et al. | |
| 9,700,868 B2 | 7/2017 | Medoff | |
| 9,777,303 B2 * | 10/2017 | Jakel | C12P 19/02 |
| 9,909,158 B2 | 3/2018 | Yamada et al. | |
| 9,920,346 B2 | 3/2018 | Funada et al. | |
| 9,926,613 B2 | 3/2018 | Kishimoto et al. | |
| 10,119,157 B2 | 11/2018 | Jakel et al. | |
| 10,233,466 B2 | 3/2019 | Redford | |
| 11,034,987 B2 | 6/2021 | Jakel et al. | |
| 11,254,955 B2 | 2/2022 | Bootsma | |
| 2006/0083823 A1 | 4/2006 | Fox et al. | |
| 2006/0251761 A1 | 11/2006 | Jansen et al. | |
| 2006/0251762 A1 | 11/2006 | Jansen et al. | |
| 2007/0014905 A1 | 1/2007 | Chen et al. | |
| 2007/0020375 A1 | 1/2007 | Jansen et al. | |
| 2008/0260902 A1 | 10/2008 | Van Houten et al. | |
| 2009/0162892 A1 * | 6/2009 | Pompejus | C12P 13/14 |
| | | | 435/67 |
| 2009/0238918 A1 | 9/2009 | Jansen et al. | |
| 2009/0258106 A1 | 10/2009 | Jansen et al. | |
| 2011/0236946 A1 | 9/2011 | Maclachlan et al. | |
| 2012/0094348 A1 | 4/2012 | Pye et al. | |
| 2012/0244590 A1 * | 9/2012 | Lee | C12M 21/12 |
| | | | 435/161 |
| 2013/0065289 A1 | 3/2013 | Carlson | |
| 2013/0236936 A1 | 9/2013 | Lee | |
| 2013/0260423 A1 | 10/2013 | Knudsen et al. | |
| 2013/0295661 A1 | 11/2013 | Roesch et al. | |
| 2014/0024064 A1 | 1/2014 | Burlew et al. | |
| 2014/0106419 A1 | 4/2014 | Bazzana et al. | |
| 2014/0193872 A1 | 7/2014 | Chen et al. | |
| 2014/0227757 A1 | 8/2014 | Jin et al. | |
| 2014/0234935 A1 | 8/2014 | Kusuda et al. | |
| 2014/0273127 A1 * | 9/2014 | Fuchs | C12P 7/06 |
| | | | 435/160 |
| 2014/0287469 A1 | 9/2014 | Medoff et al. | |
| 2014/0356915 A1 | 12/2014 | Retsina et al. | |
| 2015/0004647 A1 | 1/2015 | Niwa et al. | |
| 2015/0284745 A1 * | 10/2015 | Kozyuk | C12P 7/14 |
| | | | 435/165 |
| 2015/0344921 A1 | 12/2015 | Kacmar et al. | |
| 2016/0160242 A1 | 6/2016 | Mimitsuka et al. | |
| 2016/0186215 A1 | 6/2016 | Redford | |
| 2016/0289704 A1 | 10/2016 | Medoff | |
| 2016/0289705 A1 | 10/2016 | Medoff | |
| 2016/0289706 A1 | 10/2016 | Medoff | |
| 2016/0298141 A1 | 10/2016 | Medoff | |
| 2016/0298142 A1 | 10/2016 | Yu et al. | |
| 2016/0312258 A1 | 10/2016 | Ikeo et al. | |
| 2019/0211291 A1 | 7/2019 | Svetlichny et al. | |
| 2019/0292500 A1 | 9/2019 | Kraemer et al. | |
| 2020/0325504 A1 | 10/2020 | Van Gansberghe et al. | |
| 2021/0017547 A1 | 1/2021 | Bootsma | |
| 2021/0163996 A1 | 6/2021 | Redford | |
| 2021/0301310 A1 | 9/2021 | Jakel et al. | |
| 2021/0301311 A1 | 9/2021 | Jakel et al. | |
| 2021/0324423 A1 | 10/2021 | Redford | |

FOREIGN PATENT DOCUMENTS

| | | | | |
|---|---|---|---|---|
| WO | WO-2012075481 A | * | 6/2012 | ............... C12F 3/00 |
| WO | 2014150022 A1 | | 9/2014 | |
| WO | 2014182807 A1 | | 11/2014 | |

\* cited by examiner

SYSTEM AND METHOD FOR PRODUCING A SUGAR STREAM WITH FRONT END OIL SEPARATION

TECHNICAL FIELD

The present invention relates generally to systems and methods for use in the biochemical (e.g., biofuel), food, feed, nutrition, enzymes, amino acids, proteins, and/or pharmacy industries and, more specifically, to improved dry grind systems and methods for producing a sugar stream, such as for biochemical production.

BACKGROUND

The conventional processes for producing various types of biochemicals, such as biofuels (e.g., alcohol) and other chemicals, from grains generally follow similar procedures. Wet mill processing plants convert, for example, corn grain, into several different co-products, such as germ (for oil extraction), gluten feed (high fiber animal feed), gluten meal (high protein animal feed) and starch-based products such as alcohol (e.g., ethanol or butanol), high fructose corn syrup, or food and industrial starch. Dry grind plants generally convert grains, such as corn, into two products, namely alcohol (e.g., ethanol or butanol) and distiller's grains with solubles. If sold as wet animal feed, distiller's wet grains with solubles are referred to as DWGS. If dried for animal feed, distiller's dried grains with solubles are referred to as DDGS. This co-product provides a secondary revenue stream that offsets a portion of the overall alcohol production cost.

With respect to the wet mill process, FIG. 1 is a flow diagram of a typical wet mill alcohol (e.g., ethanol) production process 10. The process 10 begins with a steeping step 12 in which grain (e.g., corn) is soaked for 24 to 48 hours in a solution of water and sulfur dioxide in order to soften the kernels for grinding, leach soluble components into the steep water and loosen the protein matrix with the endosperm. Corn kernels contain mainly starch, fiber, protein and oil. The mixture of steeped corn and water is then fed to a degermination mill step (first grinding) 14 in which the corn is ground in a manner that tears open the kernels and releases the germ so as to make a heavy density (8.5 to 9.5 Be) slurry of the ground components, primarily a starch slurry. This is followed by a germ separation step 16 that occurs by flotation and use of a hydrocyclone(s) to separate the germ from the rest of the slurry. The germ is the part of the kernel that contains the oil found in corn. The separated germ stream, which contains some portion of the starch, protein and fiber, goes to germ washing to remove starch and protein, and then to a dryer to produce about 2.7 to 3.2 pounds (dry basis) of germ per bushel of corn (lb/bu). The dry germ has about 50% oil content on a dry basis.

The remaining slurry, which is now devoid of germ but contains fiber, gluten (i.e., protein), and starch, is then subjected to a fine grinding step (second grinding) 20 in which there is total disruption of endosperm and release of endosperm components, namely gluten and starch, from the fiber. This is followed by a fiber separation step 22 in which the slurry is passed through a series of screens in order to separate the fiber from starch and gluten and to wash the fiber clean of gluten and starch. The fiber separation stage 22 typically employs static pressure screens or rotating paddles mounted in a cylindrical screen (i.e., paddle screens). Even after washing, the fiber from a typical wet grind mill contains 15 to 20% starch. This starch is sold with the fiber as animal feed. The remaining slurry, which is now generally devoid of fiber, is subjected to a gluten separation step 24 in which centrifugation or hydrocyclones separate starch from the gluten. The gluten stream goes to a vacuum filter and dryer to produce gluten (protein) meal.

The resulting purified starch co-product then can undergo a jet cooking step 26 to start the process of converting the starch to sugar. Jet cooking refers to a cooking process performed at elevated temperatures and pressures, although the specific temperatures and pressures can vary widely. Typically, jet cooking occurs at a temperature of about 93 to 110° C. (about 200 to 230° F.) and a pressure of about 30 to 50 psi. This is followed by liquefaction 28, saccharification 30, fermentation 32, yeast recycling 34, and distillation/dehydration 36 for a typical wet mill biochemical system. Liquefaction occurs as the mixture or "mash" is held at 90 to 95° C. in order for alpha-amylase to hydrolyze the gelatinized starch into maltodextrins and oligosaccharides (chains of glucose sugar molecules) to produce a liquefied mash or slurry. In the saccharification step 30, the liquefied mash is cooled to about 50° C. and a commercial enzyme known as gluco-amylase is added. The gluco-amylase hydrolyzes the maltodextrins and short-chained oligosaccharides into single glucose sugar molecules to produce a liquefied mash. In the fermentation step 32, a common strain of yeast (*Saccharomyces cerevisae*) is added to metabolize the glucose sugars into ethanol and $CO_2$.

Upon completion, the fermentation mash ("beer") will contain about 15% to 18% ethanol (volume/volume basis), plus soluble and insoluble solids from all the remaining grain components. The solids and some liquid remaining after fermentation go to an evaporation stage where yeast can be recovered as a byproduct. Yeast can optionally be recycled in a yeast recycling step 34. In some instances, the $CO_2$ is recovered and sold as a commodity product. Subsequent to the fermentation step 32 is the distillation and dehydration step 36 in which the beer is pumped into distillation columns where it is boiled to vaporize the ethanol. The ethanol vapor is separated from the water/slurry solution in the distillation columns and alcohol vapor (in this instance, ethanol) exits the top of the distillation columns at about 95% purity (190 proof). The 190 proof ethanol then goes through a molecular sieve dehydration column, which removes the remaining residual water from the ethanol, to yield a final product of essentially 100% ethanol (199.5 proof). This anhydrous ethanol is now ready to be used for motor fuel purposes. Further processing within the distillation system can yield food grade or industrial grade alcohol.

No centrifugation step is necessary at the end of the wet mill ethanol production process 10 as the germ, fiber, and gluten have already been removed in the previous separation steps 16, 22, 24. The "stillage" produced after distillation and dehydration 36 in the wet mill process 10 is often referred to as "whole stillage" although it also is technically not the same type of whole stillage produced with a traditional dry grind process described in FIG. 2 below, since no insoluble solids are present. Other wet mill producers may refer to this type of stillage as "thin" stillage.

The wet grind process 10 can produce a high quality starch product for conversion to alcohol, as well as separate streams of germ, fiber, and protein, which can be sold as co-products to generate additional revenue streams. However, the overall yields for various co-products can be less than desirable and the wet grind process is complicated and costly, requiring high capital investment as well as high-energy costs for operation.

Because the capital cost of wet grind mills can be so prohibitive, some alcohol plants prefer to use a simpler dry grind process. FIG. 2 is a flow diagram of a typical dry grind alcohol (e.g., ethanol) production process 100. As a general reference point, the dry grind method 100 can be divided into a front end and a back end. The part of the method 100 that occurs prior to distillation 110 is considered the "front end," and the part of the method 100 that occurs after distillation 110 is considered the "back end." To that end, the front end of the dry grind process 100 begins with a grinding step 102 in which dried whole corn kernels can be passed through hammer mills for grinding into meal or a fine powder. The screen openings in the hammer mills or similar devices typically are of a size 6/64 to 9/64 inch, or about 2.38 mm to 3.57 mm, but some plants can operate at less than or greater than these screen sizes. The resulting particle distribution yields a very wide spread, bell type curve, which includes particle sizes as small as 45 microns and as large as 2 mm to 3 mm. The majority of the particles are in the range of 500 to 1200 microns, which is the "peak" of the bell curve.

After the grinding step 102, the ground meal is mixed with cook water to create a slurry at slurry step 103 and a commercial enzyme called alpha-amylase is typically added (not shown). The slurry step 103 is followed by a liquefaction step 104 whereat the pH is adjusted to about 5.2 to 5.8 and the temperature maintained between about 50° C. to 105° C. so as to convert the insoluble starch in the slurry to soluble starch. Various typical liquefaction processes, which occur at this liquefaction step 104, are discussed in more detail further below. The stream after the liquefaction step 104 has about 30% dry solids (DS) content, but can range from about 29-36%, with all the components contained in the corn kernels, including starch/sugars, protein, fiber, starch, germ, grit, oil, and salts, for example. Higher solids are achievable, but this requires extensive alpha amylase enzyme to rapidly breakdown the viscosity in the initial liquefaction step. There generally are several types of solids in the liquefaction stream: fiber, germ, and grit.

Liquefaction may be followed by separate saccharification and fermentation steps, 106 and 108, respectively, although in most commercial dry grind ethanol processes, saccharification and fermentation can occur simultaneously. This single step is referred to in the industry as "Simultaneous Saccharification and Fermentation" (SSF). Both saccharification and SSF can take as long as about 50 to 60 hours. Fermentation converts the sugar to alcohol. Yeast can optionally be recycled in a yeast recycling step (not shown) either during the fermentation process or at the very end of the fermentation process. Subsequent to the fermentation step 108 is the distillation (and dehydration) step 110, which utilizes a still to recover the alcohol.

Finally, a centrifugation step 112 involves centrifuging the residuals produced with the distillation and dehydration step 110, i.e., "whole stillage" in order to separate the insoluble solids ("wet cake") from the liquid ("thin stillage"). The liquid from the centrifuge contains about 5% to 12% DS. The "wet cake" includes fiber, of which there generally are three types: (1) pericarp, with average particle sizes typically about 1 mm to 3 mm; (2) tricap, with average particle sizes about 500 micron; (3) and fine fiber, with average particle sizes of about 250 microns. There may also be proteins with a particle size of about 45 microns to about 300 microns.

The thin stillage typically enters evaporators in an evaporation step 114 in order to boil or flash away moisture, leaving a thick syrup which contains the soluble (dissolved) solids (mainly protein and starches/sugars) from the fermentation (25 to 40% dry solids) along with residual oil and fine fiber. The concentrated slurry can be sent to a centrifuge to separate the oil from the syrup in an oil recovery step 116. The oil can be sold as a separate high value product. The oil yield is normally about 0.6 lb/bu of corn with high free fatty acids content. This oil yield recovers only about ⅓ of the oil in the corn, with part of the oil passing with the syrup stream and the remainder being lost with the fiber/wet cake stream. About one-half of the oil inside the corn kernel remains inside the germ after the distillation step 110, which cannot be separated in the typical dry grind process using centrifuges. The free fatty acids content, which is created when the oil is heated and exposed to oxygen throughout the front and back-end process, reduces the value of the oil. The (de-oil) centrifuge only removes less than 50% because the protein and oil make an emulsion, which cannot be satisfactorily separated.

The syrup, which has more than 10% oil, can be mixed with the centrifuged wet cake, and the mixture may be sold to beef and dairy feedlots as Distillers Wet Grain with Solubles (DWGS). Alternatively, the wet cake and concentrated syrup mixture may be dried in a drying step 118 and sold as Distillers Dried Grain with Solubles (DDGS) to dairy and beef feedlots. This DDGS has all the corn and yeast protein and about 67% of the oil in the starting corn material. But the value of DDGS is low due to the high percentage of fiber, and in some cases the oil is a hindrance to animal digestion and lactating cow milk quality.

Further, with respect to the liquefaction step 104, FIG. 3 is a flow diagram of various typical liquefaction processes that define the liquefaction step 104 in the dry grind process 100. Again, the dry grind process 100 begins with a grinding step 102 in which dried whole corn kernels are passed through hammer mills or similar milling systems such as roller mills, flaking mills, impacted mill, or pin mills for grinding into meal or a fine powder. The grinding step 102 is followed by the liquefaction step 104, which itself includes multiple steps as is discussed next.

Each of the various liquefaction processes generally begins with the ground grain or similar material being mixed with cook and/or backset water, which can be sent from evaporation step 114 (FIG. 2), to create a slurry at slurry tank 130 whereat a commercial enzyme called alpha-amylase is typically added (not shown). The pH is adjusted here, as is known in the art, to about 5.2 to 5.8 and the temperature maintained between about 50° C. to 105° C. so as to allow for the enzyme activity to begin converting the insoluble starch in the slurry to soluble liquid starch. Other pH ranges, such as from pH 3.5 to 7.0, may be utilized, and an acid treatment system using sulfuric acid, for example, can be used as well for pH control and conversion of the starches to sugars.

After the slurry tank 130, there are normally three optional pre-holding tank steps, identified in FIG. 3 as systems A, B, and C, which may be selected depending generally upon the desired temperature and holding time of the slurry. With system A, the slurry from the slurry tank 130 is subjected to a jet cooking step 132 whereat the slurry is fed to a jet cooker, heated to about 120° C., held in a U-tube or similar holding vessel for about 2 min to about 30 min, then forwarded to a flash tank. In the flash tank, the injected steam flashes out of the liquid stream, creating another particle size reduction and providing a means for recovering the injected stream. The jet cooker creates a sheering force that ruptures the starch granules to aid the enzyme in reacting with the starch inside the granule and allows for rapid hydration of the starch granules. It is noted here that system A may be replaced with a wet grind system. With system B, the slurry is subjected to a secondary slurry tank step 134 whereat the slurry is maintained at a temperature from about 90° C. to 100° C. for about 10 min to about 1 hour. With system C, the slurry from the slurry tank 130 is subjected to a secondary slurry tank—no steam step 136, whereat the slurry from the slurry tank 130 is sent to a secondary slurry tank, without any steam injection, and maintained at a temperature of about 80° C. to 90° C. for about 1 to 2 hours. Thereafter, the slurry from each of systems A, B, and C is forwarded, in series, to first and second holding tanks 140 and 142 for a total holding time of about 60 minutes to about 4 hours at temperatures of about 80° C. to 90° C. to complete the liquefaction step 104, which then is followed by the saccharification and fermentation steps 106 and 108, along with the remainder of the process 100 of FIG. 2. While two holding tanks are shown here, it should be understood that one holding tank, more than two holding tanks, or no holding tanks may be utilized.

In today's typical grain to biochemical plants (e.g., corn to alcohol plants), many systems, particularly dry grind systems, process the entire corn kernel through fermentation and distillation. Such designs require about 30% more front-end system capacity because there is only about 70% starch in corn, with less for other grains and/or biomass materials. Additionally, extensive capital and operational costs are necessary to process the remaining non-fermentable components within the process. By removing undesirable, unfermentable components prior to fermentation (or other reaction process), more biochemical, biofuel, and other processes become economically desirable.

Further, attempts have been made in the dry grinding industry to desirably recover high value by-products, such as oil. However, attempts to separate oil from the "hammer milled" slurry have failed because of the high concentration of solids and because the oil is not released from the solid particles. Some success has been realized with processes recovering oil from the evaporation stages of the dry mill process. However, the yield is relatively low, and the oil must move through the entire process, including fermentation, prior to evaporation. The presence of the oil in these steps of the process can be detrimental to the efficiency of the remaining parts of the process. Attempts have been made to recover the oil directly after fermentation. However, the process of mixing and fermentation emulsifies the oil, and this makes it very difficult to remove. Other attempts have been made to recover oil directly from corn by solvent extraction but the cost, for example, is too high for commercial use.

It thus would be beneficial to provide an improved dry milling system and method that produces a sugar stream, such as for biochemical production, that may be similar to the sugar stream produced by conventional wet corn milling systems, but at a fraction of the cost and generate additional revenue from high value by-products, such as oil, protein, and/or fiber, for example, with desirable yield.

SUMMARY OF THE INVENTION

The present invention provides for a dry milling system and method that produces a sugar stream, such as for biochemical production, with front end oil separation that may be similar to the sugar stream produced by conventional wet corn milling systems, but at a fraction of the cost, and generate additional revenue from high value by-products, such as oil, protein and/or fiber, for example, with desirable yield.

In one embodiment, a method for producing a sugar stream with front end oil separation is provided and includes mixing ground grain particles with a liquid to produce a slurry including starch and free oil; and subjecting the slurry to liquefaction to provide a liquefied starch solution including the free oil followed by separating the free oil from the liquefied starch solution prior to saccharification of the starch to yield an oil by product. Thereafter, the method further includes subjecting at least a portion of the liquefied starch solution to saccharification to convert the starch to simple sugars and produce a saccharified stream including the simple sugars. After saccharification but prior to further processing of the simple sugars, the method further includes separating the saccharified stream into a first solids portion and a first liquid portion including the simple sugars, wherein the first liquid portion defines a sugar stream having a dextrose equivalent of at least 20 DE and a total unfermentable solids fraction that is less than or equal to 30% of a total solids content.

In another embodiment, a system for producing a sugar stream with front end oil separation is provided and includes a slurry tank in which ground grain particles mix with a liquid to produce a slurry including starch and free oil; a liquefaction system that receives the slurry and provides a liquefied starch solution including the free oil, and whereat the starch begins to convert to oligosaccharides; and an oil separation device that is situated after the liquefaction system and separates the free oil from the liquefied starch solution to yield an oil by-product. The system further includes a saccharification system that is situated after the oil separation device and that receives at least a portion of the liquefied starch solution after the free oil is separated, the saccharification system converts the oligosaccharides to simple sugars thereby producing a saccharified stream including the simple sugars. The system also includes a first separation device that receives and separates the saccharified stream into a first solids portion and a first liquid portion including the simple sugars, wherein the first liquid portion defines a sugar stream having a dextrose equivalent of at least 20 DE and a total unfermentable solids fraction that is less than or equal to 30% of the total solids content, the first separation device situated prior to any sugar conversion device that receives and processes the simple sugars to produce a biochemical.

In another embodiment, a method for producing a sugar stream with front end oil separation is provided and includes mixing ground grain particles with a liquid to produce a slurry including starch and free oil; and subjecting the slurry to liquefaction to provide a liquefied starch solution including the starch and the free oil. The method further includes subjecting at least a portion of the liquefied starch solution to saccharification to convert the starch to simple sugars and produce a saccharified stream including the simple sugars and the free oil and, separating the free oil from the saccharified stream to yield an oil by product. Thereafter and prior to further processing of the simple sugars, the method includes separating the remaining saccharified stream into a first solids portion and a first liquid portion including the simple sugars, wherein the first liquid portion defines a sugar stream having a dextrose equivalent of at least 20 DE and a total unfermentable solids fraction that is less than or equal to 30% of a total solids content.

In another embodiment, a system for producing a sugar stream with front end oil separation is provided and includes a slurry tank in which ground grain particles mix with a liquid to produce a slurry including starch and free oil; a liquefaction system that receives the slurry and provides a liquefied starch solution including the free oil, and whereat the starch begins to convert to oligosaccharides; and a saccharification system that is situated after the liquefaction system and that receives at least a portion of the liquefied starch solution, the saccharification system converts the oligosaccharides to simple sugars thereby producing a saccharified stream including the simple sugars and the free oil. The system further includes an oil separation device that is situated after the saccharification system and separates the free oil from the saccharified stream to yield an oil by-product. Thereafter, a first separation device receives and separates the saccharified stream into a first solids portion and a first liquid portion including the simple sugars, wherein the first liquid portion defines a sugar stream having a dextrose equivalent of at least 20 DE and a total unfermentable solids fraction that is less than or equal to 30% of the total solids content, the first separation device situated prior to any sugar conversion device that receives and processes the simple sugars to produce a biochemical.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention.

DETAILED DESCRIPTION OF SPECIFIC EMBODIMENTS

Figure 1:
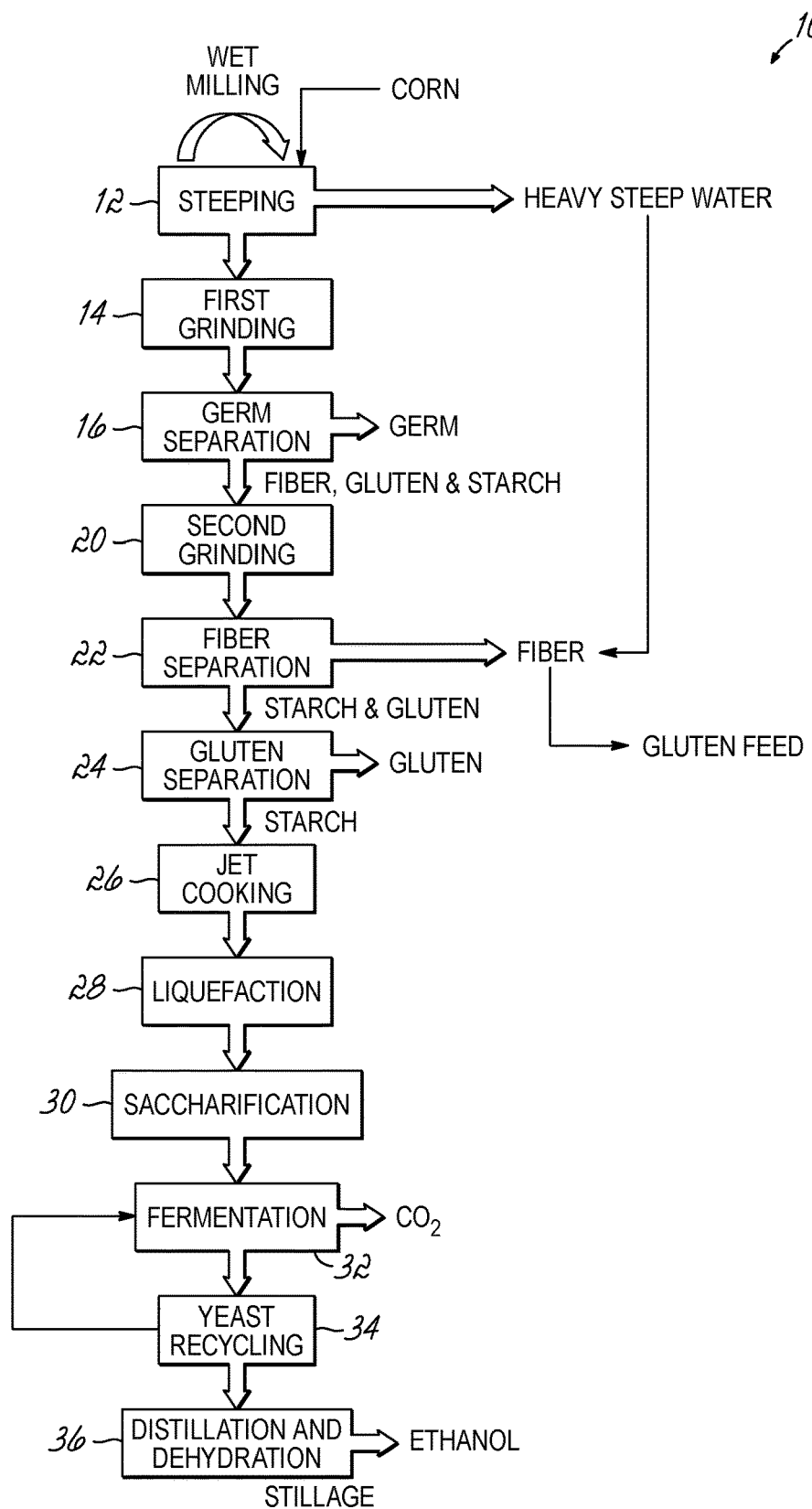
FIG. 1 is a flow diagram of a typical wet mill alcohol production process.
Figure 2:
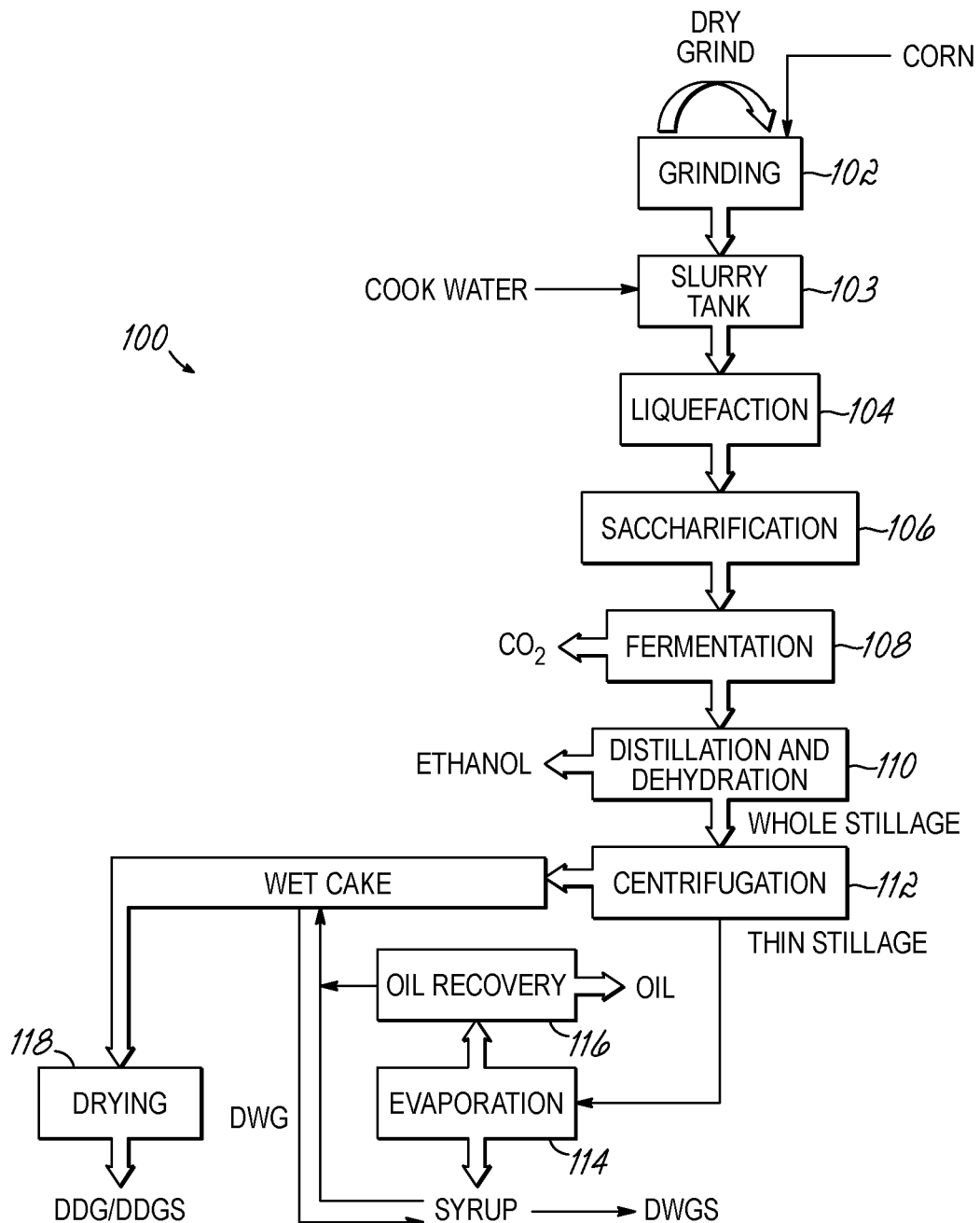
FIG. 2 is a flow diagram of a typical dry grind alcohol production process.
Figure 3:
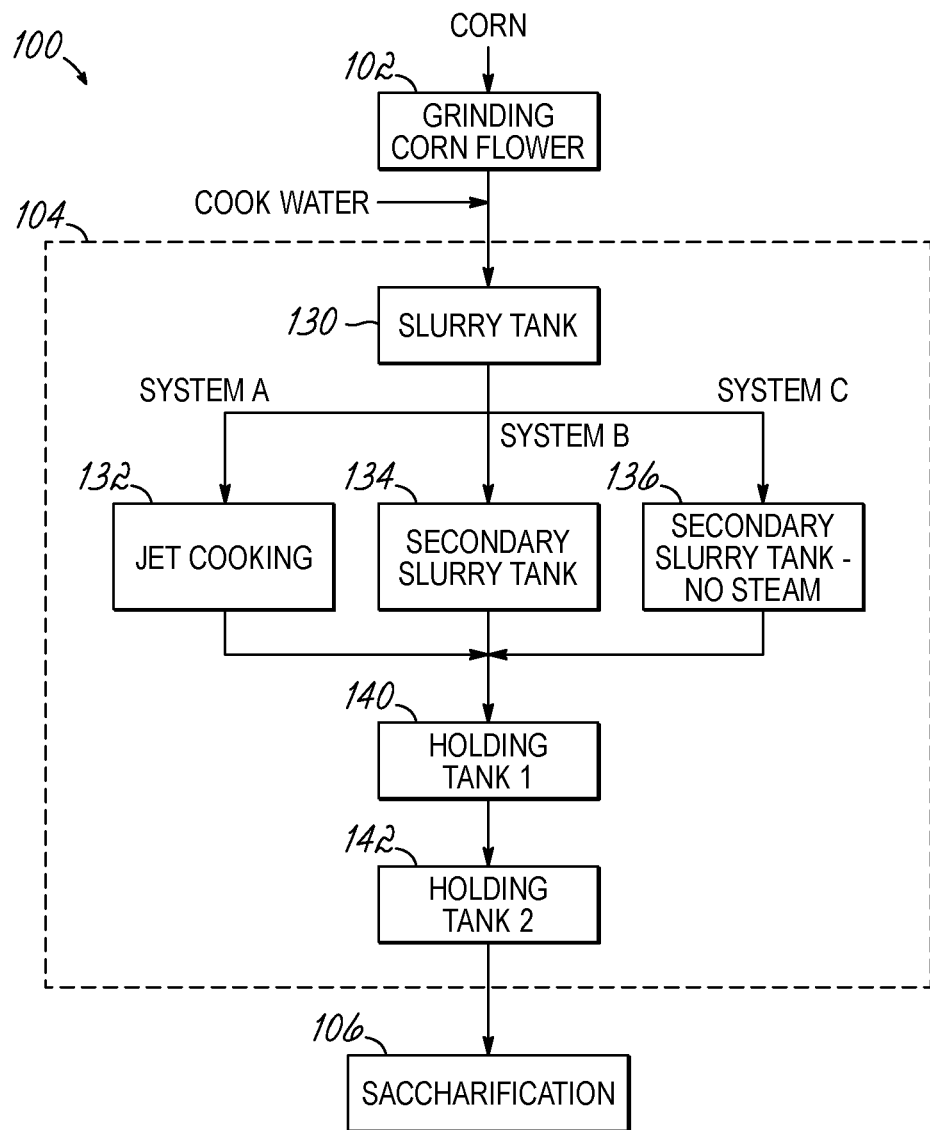
FIG. 3 is a flow diagram of various typical liquefaction processes in a typical dry grind alcohol production process.

FIGS. 1 and 2 have been discussed above and represent flow diagrams of a typical wet mill and dry grind alcohol production process, respectively. FIG. 3, likewise, has been discussed above and represents various typical liquefaction processes in a typical dry grind alcohol production process.

Figure 4:
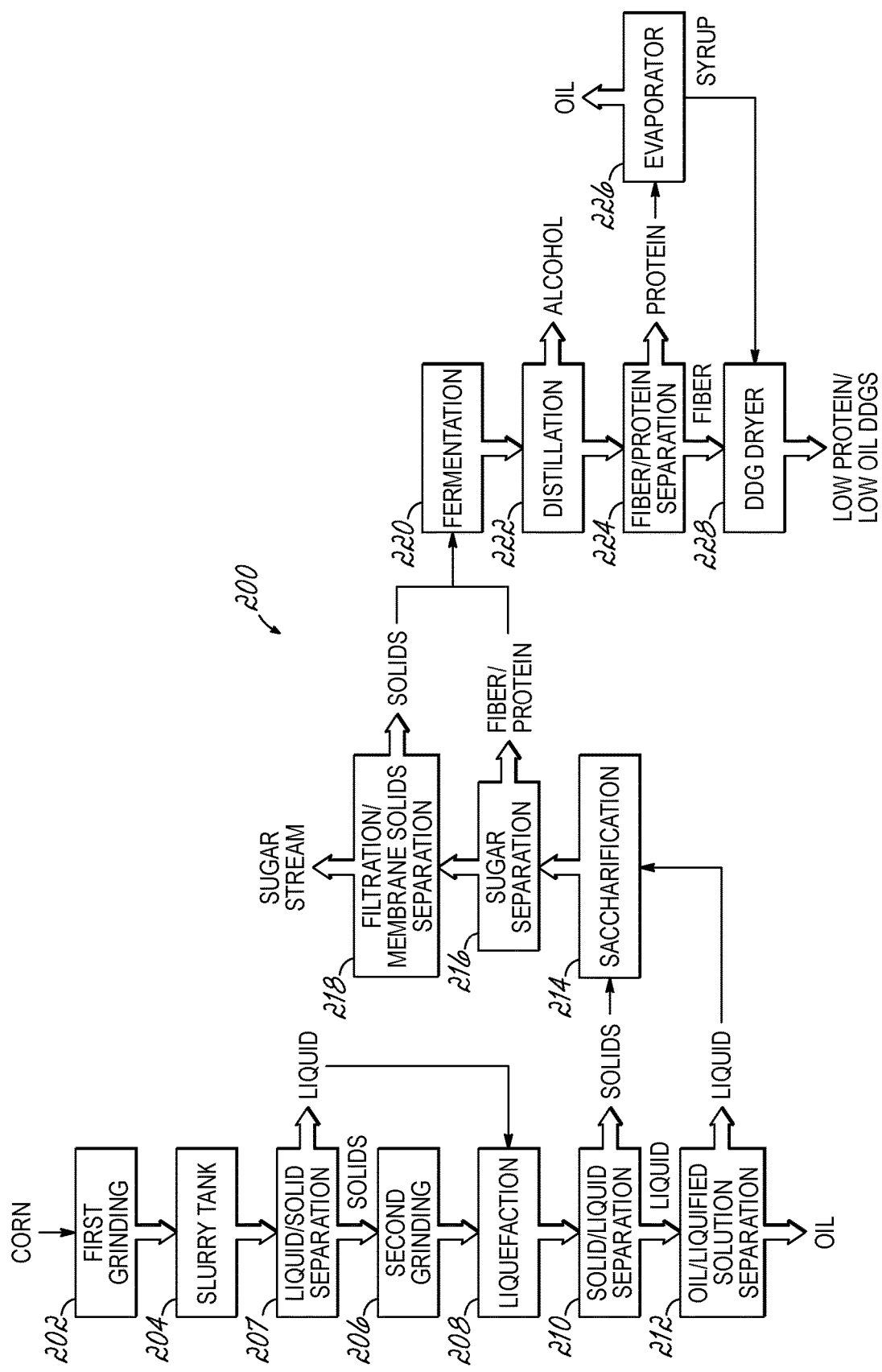
FIG. 4 is a flow diagram showing a dry grind system and method for producing a sugar stream with front end oil separation in accordance with an embodiment of the invention.
Figure 5:
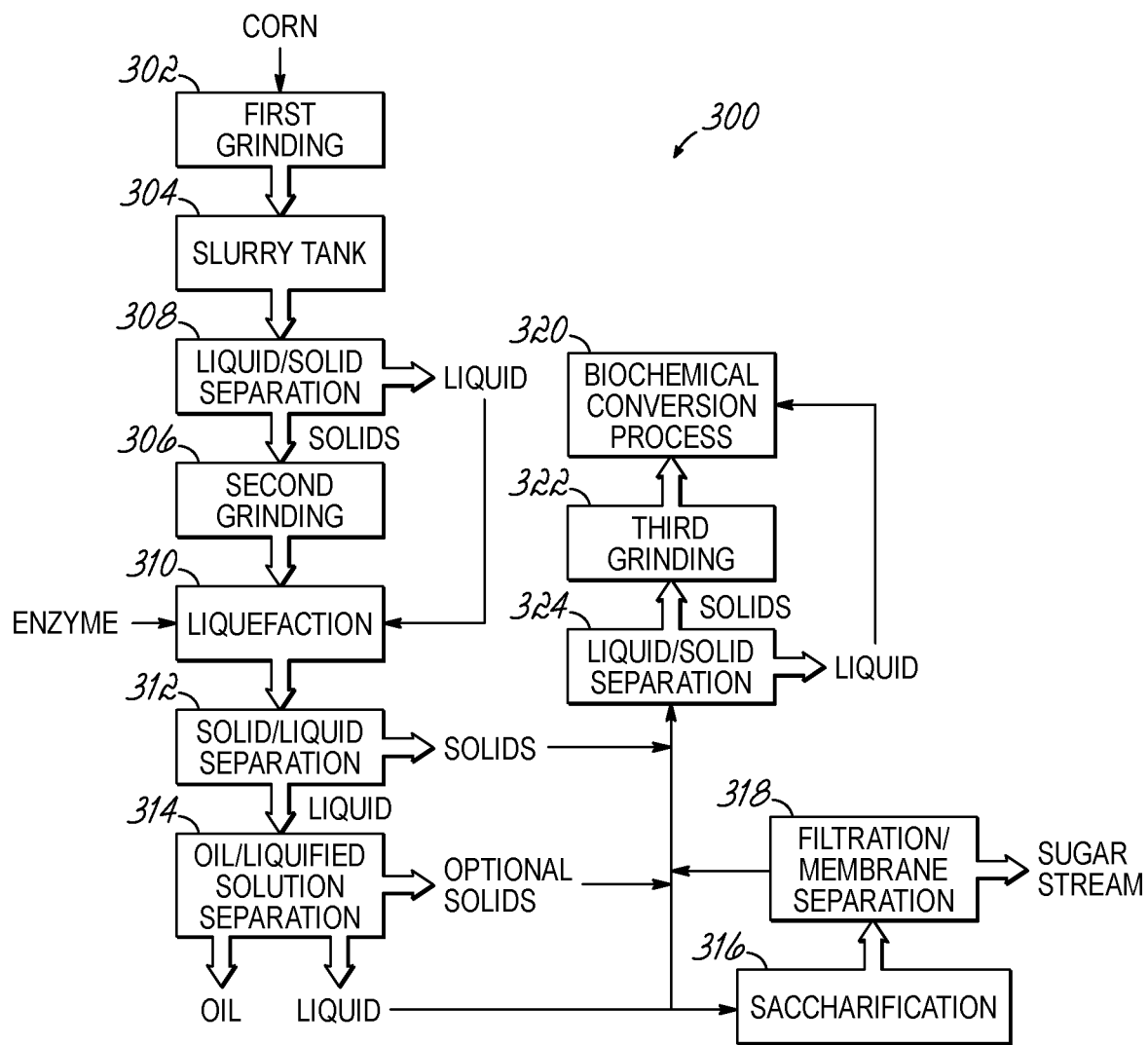
FIG. 5 is a flow diagram showing a dry grind system and method for producing a sugar stream with front end oil separation in accordance with another embodiment of the invention.
Figure 6:
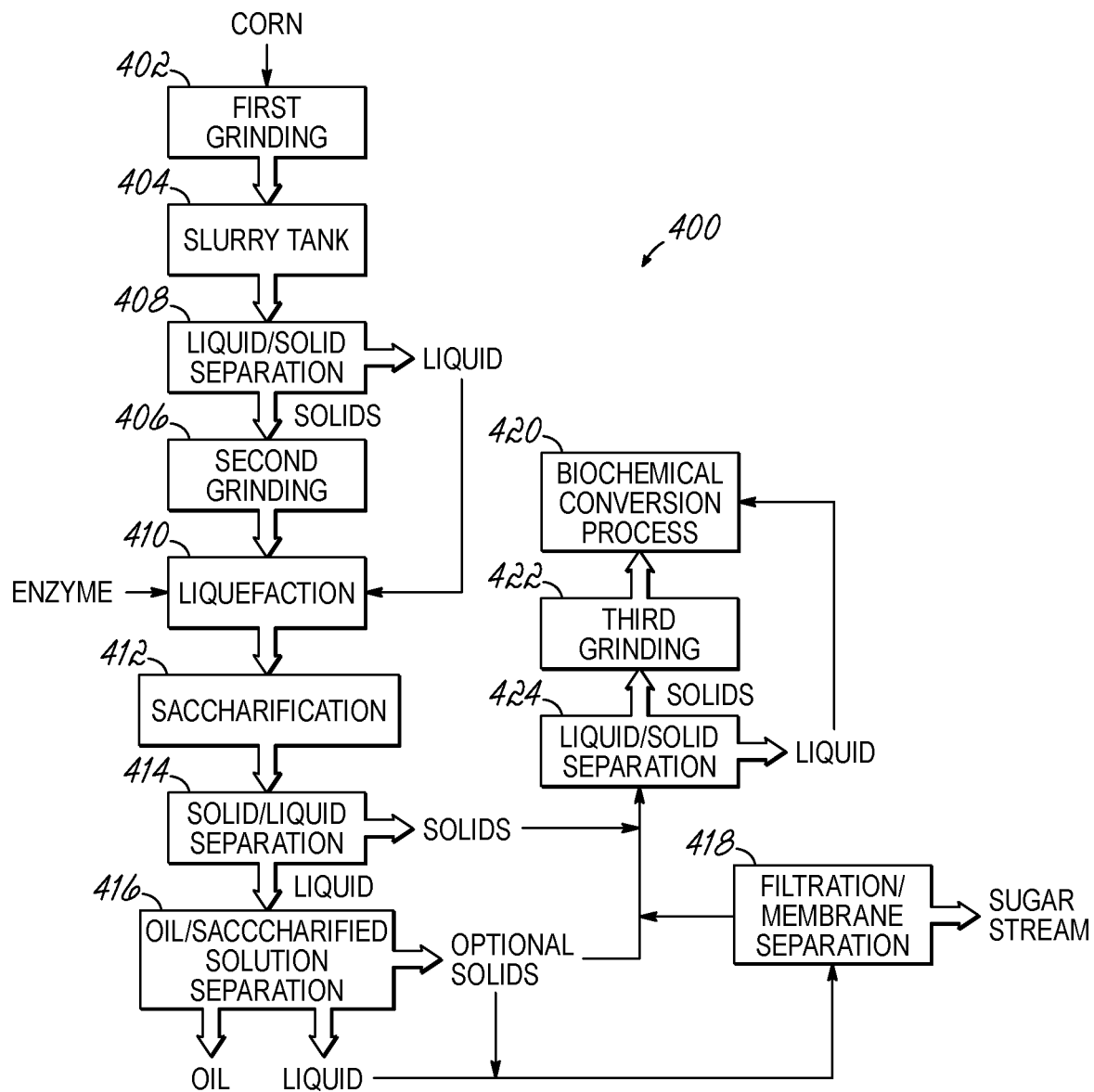
FIG. 6 is a flow diagram showing a dry grind system and method for producing a sugar stream with front end oil separation in accordance with another embodiment of the invention.

FIGS. 4, 5, and 6 illustrate embodiments of dry grind systems and methods 200, 300, 400 for producing a sugar stream from grains or similar carbohydrate sources and/or residues, such as for biochemical production, with front end oil separation in accordance with the present invention. As further discussed in detail below, a sugar/carbohydrate stream, which includes a desired Dextrose Equivalent (DE) where DE describes the degree of conversion of starch to dextrose (a.k.a. glucose) and/or has had removed therefrom an undesirable amount of unfermentable components, including in certain embodiments removing free oil prior to saccharification, can be produced after the saccharification and prior to fermentation (or other sugar utilization/conversion process), with such sugar stream being available for biochemical production, e.g., alcohol production, or other processes. In addition, the present systems and methods 200, 300, 400 also involves the removal of certain grain components, e.g., free oil prior to saccharification in certain embodiments and other corn kernel components, including protein and/or fiber, prior to fermentation or other conversion systems, as further discussed below. In other words, sugar stream production and grain component separation, including oil separation, occurs on the front end of the systems and methods 200, 300, 400.

For purposes herein, in one example, the resulting sugar stream that may be desirable after saccharification, but before fermentation, such as for use in biochemical production, can be a stream where the starch/sugars in that stream define at least a 90 DE and/or where the total insoluble (unfermentable) solids fraction of the stream is less than or equal to 7% of the total solids content in the stream. In other words, at least 90% of the total starch/sugar in that stream is dextrose and/or no greater than 7% of the total solids in that stream includes non-fermentable components. In another example, the sugar stream may define at least 95 DE. In another example, the resulting sugar stream may define at least 98 DE. In yet another example, the starch/sugars in the stream can define at least a 20, 30, 40, 50, 60, 70, or 80 DE. In another example, the total insoluble (unfermentable) solids fraction of the stream is less than or equal to 3% of the total solids content in the stream. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%. In other words, the total fermentable content (fermentable solids fraction) of the stream may be no more than 30%, 40%, 50%, 60%, 70%, 75%, 80%, 85%, 90%, 95%, 97%, or 99% of the total solids content in the stream. In another example, on a dry mass basis, the weight % fermentable material in the sugar stream that may be desired is greater than or equal to 80%. In another example, on a dry mass basis, the weight % fermentable material in a sugar stream is greater than or equal to 85%, 90%, 95%, 98%, or 99%.

In addition, although the systems and methods 200, 300, 400 described herein will generally focus on corn or kernel components, virtually any type of grain, whether whole and fractionated or any carbohydrate source, including, but not limited to, wheat, barley, sorghum, rye, rice, oats, sugar cane, tapioca, cassava, pea, or the like, as well as other biomass products, can be used. And broadly speaking, it should be understood that the entire grain or biomass or less than the entire grain, e.g., corn and/or grit and/or endosperm or biomass, may be ground and/or used in the systems and methods 200, 300, 400.

With further reference now to FIG. 4, in this dry grind system and method 200, grains such as corn and/or corn particles, for example, can be subjected to an optional first grinding step 202, which involves use of a hammer mill, roller mill, pin mill, impact mill, flaking mill, or the like, either in series or parallel, to grind the corn and/or corn particles to particle sizes less than about 7/64 inch or, in another example, less than about 10/64 inch and allow for the release of oil therefrom to define free oil. In one example, the screen size for separating the particles can range from about 24/64 inch to about 2/64 inch. In another example, the resulting particle sizes are from about 50 microns to about 3 mm. The grinding also helps break up the bonds between the fiber, protein, starch, and germ. In one example, screen size or resulting particle size may have little to no impact on the ability to separate the sugar from the remaining kernel or similar raw material component(s). If the carbohydrate source is pre-ground or initially in particulate form, the optional grind step 202 may be excluded from the system and method 200.

Next, the ground corn flour is mixed with backset liquid at slurry tank 204 to create a slurry. Optionally, fresh water may be added so as to limit the amount of backset needed here. An enzyme(s), such as alpha amylase, optionally can be added to the slurry tank 204 or in a slurry blender (not shown) between the first grinding step 202 and the slurry tank 204. The slurry may be heated at the slurry tank 204 from about 66° C. (150° F.) to about 93° C. (200° F.) for about 10 min to about 120 min. The stream from the slurry tank 204 contains about 0.5 lb/bu free oil, about 1.5 lb/bu germ (particle size ranges from about 50 microns to about 3 mm), about 1.8 lb/bu grit (particle size ranges from about 50 microns to about 3 mm), which can include starch, and about 4.25 lb/bu fiber (particle size ranges from about 50 microns to about 3 mm).

The stream from the slurry tank 204 next may be subjected to an optional second grinding/particle size reduction step 206, which may involve use of a disc mill, hammer mill, a pin or impact mill, a roller mill, a grind mill, or the like, to further grind the corn particles to particle sizes less than about 850 microns and allow for additional release of oil and protein/starch complexes therefrom. In another example, the particle sizes are from about 300 microns to about 650 mm. The grinding further helps continue to break up the bonds between the fiber, protein, and starch and facilitates the release of free oil from germ particles. The stream from the second grinding/particle size reduction step 206 contains about 0.1 lb/bu to about 1.0 lb/bu free oil.

Prior to subjecting the stream from the slurry tank 204 to the optional second grinding/particle size reduction step 206, the slurry may be subjected to an optional liquid/solid separation step 207 to remove a desired amount of liquids therefrom. The liquid/solid separation step 207 separates a generally liquefied solution (about 60% to about 80% by volume), which includes free oil, protein, and fine solids (which do not need grinding), from heavy solids cake (about 20% to about 40% by volume), which includes the heavier fiber, grit, and germ, which can include bound oil, protein, and/or starch. The liquid/solid separation step 308 uses dewatering equipment, e.g., a paddle screen, a vibration screen, screen decanter centrifuge or conic screen centrifuge, a pressure screen, a preconcentrator, a filter press, or the like, to accomplish separation of the solids from the liquid portion. The fine solids can be no greater than 200 microns. In another example, the fine solids are no greater than 500 microns, which is generally dependent upon the screen size openings used in the liquid/solid separation device(s).

In one example, the dewatering equipment is a paddle screen, which includes a stationary cylinder screen with a high speed paddle with rake. The number of paddles on the paddle screen can be in the range of 1 paddle per 4 to 8 inches of screen diameter. In another example, the dewatering equipment is a preconcentrator, which includes a stationary cylinder screen with a low speed screw conveyor. The conveyor pitch on the preconcentrator can be about 1/6 to about 1/2 of the screen diameter. The number of paddles on the paddle screen and the conveyor pitch on the preconcentrator can be modified depending on the amount of solids in the feed. The gap between the paddle screen and paddle can range from about 0.04 to about 0.2 inch. A smaller gap gives a drier cake with higher capacity and purer fiber but loses more fiber to filtrate. A larger gap gives a wetter cake with lower capacity and purer liquid (less insoluble solid). The paddle speed can range from 400 to 1200 RPM. In another example, the paddle speed can range from 800 to 900 RPM. A higher speed provides higher capacity but consumes more power. One suitable type of paddle screen is the FQ-PS32 paddle screen, which is available from Fluid-Quip, Inc. of Springfield, Ohio.

The screen for the dewatering equipment can include a wedge wire type with slot opening, or a round hole, thin plate screen. The round hole screen can help prevent long fine fiber from going through the screen better than the wedge wire slot opening, but the round hole capacity is lower, so more equipment may be required if using round hole screens. The size of the screen openings can range from about 45 microns to about 500 microns. In another example, the screen openings can range from 100 to 300 microns. In yet another example, the screen openings can range from 200 to 250 microns. Smaller screen openings tend to increase the protein/oil/alcohol yield with higher equipment and operation cost, whereas larger screen openings tend to lower protein/oil/alcohol yield with less equipment and operation cost.

The wet cake or dewatered solids portion of the stream at the liquid/solid separation step 207 (about 60% to about 65% water) next may be subjected to the optional second grinding/particle size reduction step 206, as described above. After milling, the solids can be mixed with the liquefied starch solution from the liquid/solid separation step 207, as shown, to form a heavy slurry and subjected to liquefaction step 208.

In particular, the liquefaction step 208 can include multiple steps as discussed above and shown in FIG. 3. In one embodiment, the pH can be adjusted here to about 5.2 to about 5.8 and the temperature maintained between about 50° C. to about 105° C. so as to convert the insoluble starch in the slurry to soluble or liquid starch. Other pH ranges, such as from pH 3.5-7.0, may be utilized and an acid treatment system using sulfuric acid, for example, may be used as well for pH control and for conversion of the starches to sugars. The slurry may be further subjected to jet cooking whereat the slurry is fed to a jet cooker, heated to about 120° C., held for about 2 min to about 30 min, then forwarded to a flash tank. The jet cooker creates a sheering force that ruptures the starch granules to aid the enzyme in reacting with the starch inside the granule and for hydrating the starch molecules. In another embodiment, the slurry can be subjected to a secondary slurry tank whereat steam is injected directly to the secondary slurry tank and the slurry is maintained at a temperature from about 80° C. to about 100° C. for about 30 min to about one hour. In yet another embodiment, the slurry can be subjected to a secondary slurry tank with no steam. In particular, the slurry is sent to a secondary slurry tank without any steam injection and maintained at a temperature of about 80° C. to about 90° C. for 1 to 2 hours. Thereafter, the liquefied slurry may be forwarded to a holding tank for a total holding time of about 1 hour to about 4 hours at temperatures of about 80° C. to about 90° C. to complete the liquefaction step 208. With respect to the liquefaction step 208, pH, temperature, and/or holding time may be adjusted as desired.

The slurry stream after the liquefaction step 208 has about 28% to about 36% dry solids (DS) content with all the components contained in the corn kernels, including starches/sugars, protein, fiber, germ, grit, oil, and salts, for example. There generally are three types of solids in the liquefaction stream: fiber, germ, and grit, which can include starch and protein, with all three solids having about the same particle size distribution. The stream from the liquefaction step 208 contains about 1 lb/bu free oil, about 1.5 lb/bu germ particle (size ranges from less about 50 microns to about 1 mm), about 4.5 lb/bu protein (size ranges from about 50 microns to about 1 mm), and about 4.25 lb/bu fiber (particle size ranges from about 50 microns to about 3 mm).

After the liquefaction step 208 (but before any potential saccharification, fermentation, or other processing of the sugar stream), so as to provide a more desirable sugar stream, the liquefied sugar stream can be subjected to a solid/liquid separation step 210 followed by an oil/liquefied starch solution separation step 212. In particular, the solid/liquid separation step 210, which may be optional, uses any suitable filtration device, e.g., a pre-concentrator, paddle screen, pressure screen, fiber centrifuge, decanter, and the like, to separate the liquid from the solid material. The screen openings can range from about 50 microns to about 500 microns and will be selected to desirably separate the fiber, grit, and germ particles from the liquid, which primarily includes the liquefied starch solution with small amounts of oil, free protein (mainly gluten), and starch. In one example, the screen openings are about 50 microns.

The liquid portion may be subjected to the oil/liquefied starch solution separation step 212 whereat the liquid portion is subjected to an oil recovery device to separate out the oil before sending the liquefied starch solution to meet up with the solids portion from the solid/liquid separation step 210 prior to fermentation, such as at saccharification step 214, which is discussed below. The oil/liquefied starch solution separation step 212 can use any type of oil separation device, such as a mud centrifuge, two or three phase decanter, disc decanter, two or three phase disc centrifuge, flotation tank, dissolved air flotation tank/system, and the like, to separate oil from the sugar stream by taking advantage of density differences. At oil/liquefied starch solution separation step 212, the liquefied starch solution is used as heavy media liquid to float the oil, which has a density of about 1.05 grams/cc to about 1.15 grams/cc. The oil that is recovered at this stage in the process has a much more desirable quality in terms of color and free fatty acid content (from about 2% to about 5%) as compared to oil that is recovered downstream, particularly oil recovered after saccharification and fermentation. In particular, the color of the pre-saccharification recovered oil is lighter in color and lower in free fatty acid content. The oil yield can include 0.1 lb/bu or greater. In one example, the oil yield is from about 0.1 lb/bu to about 0.6 lb/bu, or greater than about 0.6 lb/bu. In another example, the oil yield is from about 0.2 to about 1.0 lb/bu, or greater than about 1.0 lb/bu.

The separated solids portion from the solid/liquid separation step 210, along with the liquefied starch solution from the oil/liquefied starch solution separation step 212, can be sent to the saccharification step 214 whereat complex carbohydrate and oligosaccharides are further broken down into simple sugars, particularly single glucose sugar molecules (i.e., dextrose) to produce a liquefied mash. Optionally, a portion or the entirety of the separated solids portion from the solid/liquid separation step 210 and/or the liquefied starch solution from the oil/liquefied starch solution separation step 212 can be sent to fermentation step 220 or another conversion step.

In particular, at the saccharification step 214, the slurry stream may be subjected to a two-step conversion process. The first part of the cook process, in one example, includes adjusting the pH to about 3.5 to about 7.0, with the temperature being maintained between about 30° C. to about 100° C. for 1 to 6 hours to further convert the insoluble starch in the slurry to soluble starch, particularly dextrose. In another example, the pH can be 5.2 to 5.8 or 5.5, for example. In another example, the temperature can be maintained at 80° C. for about 5 hours. Also, an enzyme, such as alpha-amylase may be added here. In one example, the amount of alpha-amylase may be from about 0.0035 wt % to about 0.04 wt % of the slurry stream. In another example, the amount of alpha-amylase may be from about 0.02 wt % to about 0.1 wt % of the total stream.

The second part of the cook process, in one example, may include adjusting the pH to about 3.5 to 5.0, with the temperature being maintained between about 30° C. to about 100° C. for about 10 minutes to about 5 hours so as to further convert the insoluble starch in the slurry to soluble starch, particularly dextrose. In another example, the pH can be 4.5. In another example, the temperature can be maintained from about 54° C. (130° F.) to about 74° C. (165° F.) for about 4 hours or up to about 60 hours. An enzyme, such as glucoamylase, also may be added here. In one example, the amount of glucoamylase may be from about 0.01 wt % to about 0.2 wt % of the slurry stream. In another example, the amount of glucoamylase may be from about 0.08 to about 0.14 wt % of the slurry stream. Other enzymes or similar catalytic conversion agents may be added at this step or previous steps that can enhance starch conversion to sugar or yield other benefits, such as fiber or cellulosic sugar release, conversion of proteins to soluble proteins, or the release of oil from the germ.

A saccharified sugar stream having a density of about 1.05 grams/cc to about 1.15 grams/cc can result here. At this point, the saccharified sugar stream may be no less than about 90 DE. In another example, the saccharified sugar stream may be no less than 20, 30, 40, 50, 60, 70, or 80 DE. In this example, the saccharified sugar stream may not be considered desirable or "clean" enough, such as for use in biochemical (e.g., biofuel) production, because the total fermentable content of the stream may be no more than 75% of the total solids content in the stream. In this example, the saccharified sugar stream can have a total solids fraction of about 25% to about 40%, such solids including sugar, starch, fiber, protein, germ, oil, and ash, for example. In yet another example, the total fermentable content of the stream is no more than 30, 40, 50, 60, or 70% of the total solids content in the stream. The remaining solids are fiber, protein, oil, and ash, for example. The stream from the saccharification step 214 contains about 0.1 lb/bu to about 1.0 lb/bu free oil.

After the saccharification step 214 (but before any potential fermentation or processing of the sugar stream), so as to provide a more desirable sugar stream, the saccharified sugar stream can be subjected to an optional sugar separation step 216. The sugar separation step 216 filters a generally liquefied solution (about 60 to about 80% by volume), which includes sugar, free oil, protein, fine solids, fiber, grit and germ, and which has a total solids fraction of about 30%, with a range of about 20% to about 40%, but higher or low solids fractions can be produced, but may not be economical here. In particular, the sugar separation step 216 includes a clarifier, 2 or 3 phase separator, filtration centrifuge, drum filter, dissolved air flotation, paddle screen, pressure screen, or the like to accomplish substantial separation of the solids portion, primarily fiber, germ, grit, which can include protein, from the liquid sugar portion, which primarily includes sugar (e.g., dextrose), residual oil, and fine solids. The solids portion, which has a total solids fraction of about 39% or that is in a range of about 25% to about 50%, may be sent on to the fermentation step 220.

At this point, the separated sugar stream may be no less than about 90 DE. In another example, the liquefied sugar stream may be no less than 20, 30, 40, 50, 60, 70, or 80 DE. In this example, the sugar stream here may be considered desirable or "clean" enough, such as for use in biochemical production, because the total insoluble (unfermentable) solids fraction of the stream is less than or equal to 10% of the total solids of the stream. In another example, the total insoluble (unfermentable) solids fraction of the stream is less than or equal to 7%. In another example, the total insoluble (unfermentable) solids fraction of the stream is less than or equal to 5%. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%. In this example, the stream sent to sugar separation step 216 may have a total solids fraction of about 27%, or in a range of about 20% to about 35%, such solids including sugar, starch, fiber, protein and/or germ, for example.

After the optional sugar separation step 216, the sugar stream may be subjected to an optional microfiltration (or similar filtration) step 218, which can include a rotary vacuum filter, micro-filter, membrane filtration, precoat/diatomaceous earth filter, or the like, to produce a more desirable sugar stream, which may be considered a purified or refined sugar stream, by further separating out any remaining insoluble components, color, ash, minerals, or the like. In one example, the filter screen size here may be from about 0.1 micron to about 100 microns. In another example, the filter screen size may be from about 5 microns to about 50 microns. Due to the input of water, the sugar stream can have a total solids fraction of 20-35%. In this example, the sugar stream here may be considered purified or refined enough because the total insoluble (unfermentable) solids fraction of the stream is less than 10%. In another example, the total insoluble (unfermentable) solids fraction of the stream is less than or equal to 5%. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%.

The microfiltration step 218 may be replaced by, or additionally include, ultrafiltration, carbon column color removal, filter press, flotation, adsorption, and/or demineralization technologies (e.g., ion exchange). Resin refining, which includes a combination of carbon filtration and demineralization in one step, can also be utilized for refining the sugars. Additionally, due to a low solids content of the sugar stream here, an optional evaporation step (not shown) may be added hereafter to further concentrate the total solids fraction.

The sugar stream from the microfiltration step 218 can be sent on to a further processing step, such as a fermentation step where the sugars are converted, e.g., via a fermenter, to alcohol, such as ethanol or butanol or any other fermentation conversion process or similar sugar utilization/conversion process, followed by distillation and/or separation of the desired component(s) (not shown), which can recover the alcohol or byproduct(s)/compound(s) produced, as is known in the art. The sugar stream can allow for recovery of a fermentation agent from the fermentation step. The fermentation agent can be recovered by means known in the art and can be dried as a separate product or, for example, can be sent to a protein separation step or other streams/steps, in the system and method 200, which can allow for capture of the fermentation agent and/or used for further processing. Fermentation agent (such as yeast or bacteria) recycling can occur by use of a clean sugar source. Following distillation or desired separation step(s), the system and method 200 can include any back end type process(es), which may be known or unknown in the art to process, for example, the whole stillage. The fermentation step may be part of an alcohol production system that receives a sugar stream that is not as desirable or clean, i.e., "dirtier," than the sugar stream being sent and subjected to the same fermentation step as the dirty sugar stream. Other options for the sugar stream, aside from fermentation, can include further processing or refining of the glucose to fructose or other simple or even complex carbohydrate, processing into feed, microbe based fermentation (as opposed to yeast based) and other various chemical, pharmaceutical or nutraceutical processing (such as propanol, isobutanol, citric acid or succinic acid), and the like. Such processing can occur via a reactor, including, for example, a catalytic or chemical reactor. In one example, the reactor is a fermenter.

Still referring to FIG. 4, the solid or heavy components from the sugar separation step 216 and microfiltration step 218 can be combined together and sent to fermentation step 220. These heavier components or underflow, can be more concentrated in total solids, at about 28%. The fermentation step 220 is followed by distillation 222. At the distillation tower, the fermented solution is separated from the stillage, which includes fiber, protein, and germ particles, to produce alcohol. The fiber can be separated from the germ particles and protein (gluten) at a fiber/protein separation step 224 by differences in particle sizes using a screen device, such as a filtration centrifuge, to remove the fiber therefrom. The screen openings normally will be about 500 microns to capture amounts of tipcap, pericarp, as well as fine fiber, but can range from about 200 microns to about 1,000 microns. The separated fiber is used to produce a low protein (less than about 25%)/low oil (less than about 8%) DDG.

If a lower protein and oil content in the fiber is needed or desired, the fiber may be sent to a holding tank (not shown), for example, whereat the pH of the separated fiber can be adjusted to about 8 to about 10.5 (or about 8 to about 9.5), such as by the addition of chemicals, e.g., sodium hydroxide, lime, sodium carbonate, trisodium phosphate, or the like to help release additional oil from the germ. Also, cell wall breaking enzymes, e.g., protease and the like, and/or chemicals, e.g., sodium sulfite and the like, may be added here to help release additional oil from the germ. In one example, the fiber can be held in the tank for about 1 hour at a temperature of about 140° F. to about 200° F. (or about 180° F. to about 200° F.). Thereafter, the fiber can be subjected to a grind step to release more oil and protein from the fiber. The fiber produced by these additional treatment steps can give a much lower oil (less than 2%) and lower protein (less than 10%) and can be used for secondary alcohol production.

The centrate from the fiber/protein separation step 224 goes to an evaporator 226 to separate any oil therefrom and to produce syrup, which can be mixed with the DDG and dried, as represented by numeral 228, to give the low protein (less than about 25%)/low oil (less than about 8%) DDGS, such as for cows or pigs, particularly dairy cows. The DDGS contains less than about 25% protein, less than about 8% oil, and less than about 5% starch.

In addition, an optional centrifugation step (not shown) may be provided to recover the xanthophyll content in the emulsion layer of the recovered oils, both prior to and after saccharification 214, and mixed with the protein by-product prior to drying to increase the feed value. The overflow from the centrifuge(s) can go back to the oil storage tanks (not shown).

With further reference now to FIG. 5, in this dry grind system and method 300, grains such as corn and/or corn particles, for example, can be subjected to an optional first grinding step 302, which involves use of a hammer mill, roller mill, pin mill, impact mill, flaking mill, or the like, either in series or parallel, to grind the corn and/or corn particles to particle sizes less than about $7/64$ inch or, in another example, less than about $10/64$ inch and allow for the release of oil therefrom defining free oil. In one example, the screen size for separating the particles can range from about $24/64$ inch to about $2/64$ inch. In another example, the resulting particle sizes are from about 50 microns to about 3 mm. The grinding also helps break up the bonds between the fiber, protein, starch, and germ. In one example, screen size or resulting particle size may have little to no impact on the ability to separate the sugar from the remaining kernel or similar raw material component(s). If the carbohydrate source is pre-ground or initially in particulate form, the optional grind step 302 may be excluded from the system and method 300.

Next, the ground corn flour is mixed with backset liquid at slurry tank 304 to create a slurry. Optionally, fresh water may be added so as to limit the amount of backset needed here. An enzyme(s), such as alpha amylase, optionally can be added to the slurry tank 304 or in a slurry blender (not shown) between the optional first grinding step 302 and the slurry tank 304. The slurry may be heated at the slurry tank 304 from about 66° C. (150° F.) to about 93° C. (200° F.) for about 10 min to about 120 min. The stream from the slurry tank 304 contains about 0.5 lb/bu free oil, about 1.5 lb/bu germ (particle size ranges from about 50 microns to about 3 mm), about 1.8 lb/bu grit (particle size ranges from about 50 microns to about 3 mm), which can include starch, and about 4.25 lb/bu fiber (particle size ranges from about 50 microns to about 3 mm).

The stream from the slurry tank 304 next may be subjected to an optional second grinding/particle size reduction step 306, which may involve use of a disc mill, hammer mill, a pin or impact mill, a roller mill, a grind mill, or the like, to further grind the corn particles to particle sizes less than about 850 microns and allow for additional release of oil and protein/starch complexes therefrom. In another example, the particle sizes are from about 300 microns to about 650 mm. The grinding further helps continue to break up the bonds between the fiber, protein, and starch and facilitates the release of free oil from germ particles. The stream from the second grinding/particle size reduction step 306 contains about 0.1 lb/bu to about 1.0 lb/bu free oil.

Prior to subjecting the stream from the slurry tank 304 to the optional second grinding/particle size reduction step 306, the slurry may be subjected to an optional liquid/solid separation step 308 to remove a desired amount of liquids therefrom. The liquid/solid separation step 308 separates a generally liquefied solution (about 60% to about 80% by volume), which includes free oil, protein, and fine solids (which do not need grinding), from heavy solids cake (about 20% to about 40% by volume), which includes the heavier fiber, grit, and germ, which can include bound oil, protein, and/or starch. The liquid/solid separation step 308 uses dewatering equipment, e.g., a paddle screen, a vibration screen, screen decanter centrifuge or conic screen centrifuge, a pressure screen, a preconcentrator, a filter press, or the like, to accomplish separation of the solids from the liquid portion. The fine solids can be no greater than 200 microns. In another example, the fine solids are no greater than 500 microns, which is generally dependent upon the screen size openings used in the liquid/solid separation device(s).

In one example, the dewatering equipment is a paddle screen, which includes a stationary cylinder screen with a high speed paddle with rake. The number of paddles on the paddle screen can be in the range of 1 paddle per 4 to 8 inches of screen diameter. In another example, the dewatering equipment is a preconcentrator, which includes a stationary cylinder screen with a low speed screw conveyor. The conveyor pitch on the preconcentrator can be about $1/6$ to about $1/2$ of the screen diameter. The number of paddles on the paddle screen and the conveyor pitch on the preconcentrator can be modified depending on the amount of solids in the feed. The gap between the paddle screen and paddle can range from about 0.04 to about 0.2 inch. A smaller gap gives a drier cake with higher capacity and purer fiber but loses more fiber to filtrate. A larger gap gives a wetter cake with lower capacity and purer liquid (less insoluble solid). The paddle speed can range from 400 to 1200 RPM. In another example, the paddle speed can range from 800 to 900 RPM. A higher speed provides higher capacity but consumes more power. One suitable type of paddle screen is the FQ-PS32 paddle screen, which is available from Fluid-Quip, Inc. of Springfield, Ohio.

The screen for the dewatering equipment can include a wedge wire type with slot opening, or a round hole, thin plate screen. The round hole screen can help prevent long fine fiber from going through the screen better than the wedge wire slot opening, but the round hole capacity is lower, so more equipment may be required if using round hole screens. The size of the screen openings can range from about 45 microns to about 500 microns. In another example, the screen openings can range from 100 to 300 microns. In yet another example, the screen openings can range from 200 to 250 microns. Smaller screen openings tend to increase the protein/oil/alcohol yield with higher equipment and operation cost, whereas larger screen openings tend to lower protein/oil/alcohol yield with less equipment and operation cost.

The wet cake or dewatered solids portion of the stream at the liquid/solid separation step 308 (about 60% to about 65% water) next may be subjected to the optional second grinding/particle size reduction step 306, as described above. After milling, the solids can be mixed with the liquefied starch solution from the liquid/solid separation step 308, as shown, to form a heavy slurry then subjected to liquefaction step 310.

In particular, the liquefaction step 310 itself can include multiple steps as discussed above and shown in FIG. 3. In one embodiment, the pH can be adjusted here to about 5.2 to about 5.8 and the temperature maintained between about 50° C. to about 100° C. so as to convert the insoluble starch in the slurry to soluble or liquid starch. Other pH ranges, such as from pH 3.5 to 7.0, may be utilized and an acid treatment system using sulfuric acid, for example, may be used as well for pH control and for conversion of the starches to sugars. The slurry may be further subjected to jet cooking whereat the slurry is fed to a jet cooker, heated to about 120° C., held for about 2 min to about 30 min, then forwarded to a flash tank. The jet cooker creates a sheering force that ruptures the starch granules to aid the enzyme in reacting with the starch inside the granule and for hydrating the starch molecules. In another embodiment, the slurry can be subjected to a secondary slurry tank whereat steam is injected directly to the secondary slurry tank and the slurry is maintained at a temperature from about 80° C. to about 100° C. for about 30 min to about one hour. In yet another embodiment, the slurry can be subjected to a secondary slurry tank with no steam. In particular, the slurry is sent to a secondary slurry tank without any steam injection and maintained at a temperature of about 80° C. to about 90° C. for 1 to 2 hours. Thereafter, the liquefied slurry may be forwarded to a holding tank for a total holding time of about 1 hour to about 4 hours at temperatures of about 80° C. to about 90° C. to complete the liquefaction step 310. With respect to the liquefaction step 310, pH, temperature, and/or holding time may be adjusted as desired.

The slurry stream after the liquefaction step 310 has about 25% to about 36% dry solids (DS) content with all the components contained in the corn kernels, including starches/sugars, protein, fiber, germ, grit, oil, and salts, for example. There generally are three types of solids in the liquefaction stream: fiber, germ, and grit, which can include starch and protein, with all three solids having about the same particle size distribution. The stream from the liquefaction step 310 contains about 1 lb/bu free oil, about 1.5 lb/bu germ particle (size ranges from less about 50 microns to about 1 mm), about 4.5 lb/bu protein (size ranges from about 50 microns to about 1 mm), and about 4.25 lb/bu fiber (particle size ranges from about 50 microns to about 3 mm).

After the liquefaction step 310 (but before any potential saccharification, fermentation, or other processing of the sugar stream), so as to provide a more desirable sugar stream, the liquefied sugar stream can be subjected to a solid/liquid separation step 312 and an oil/liquefied starch solution separation step 314. In particular, the solid/liquid separation step 312 uses any suitable filtration device, e.g., a pre-concentrator, paddle screen, pressure screen, fiber centrifuge, decanter, and the like, to separate the liquid from the solid material. The screen openings can range from about 20 microns to about 500 microns and will be selected to desirably separate the fiber, grit, and germ particles from the liquid, which primarily includes the liquefied starch solution with small amounts of oil, free protein (mainly gluten), and starch. In one example, the screen openings are about 20 microns. In another example, the screen openings are about 50 microns.

The liquid portion can go to the oil/liquefied starch solution separation step 314 whereat the liquid portion can be subjected to an oil separation device to separate out the oil before sending the liquefied starch solution to the saccharification step 316, which is discussed below. The oil/liquefied starch solution separation step 314 can use any type of oil separation device, such as a mud centrifuge, two or three phase decanter, disc decanter, two or three phase disc centrifuge, flotation tank, dissolved air flotation tank/system, and the like, to separate oil from the sugar stream by taking advantage of density differences. With a three-phase device, such as a three phase centrifuge or decanter, a heavier solids portion optionally can be separated out the oil/liquified starch solution step 314 from the oil and liquified starch solution. At oil/liquefied starch solution separation step 314, the liquefied starch solution is used as heavy media liquid to float the oil, which has a density of about 1.05 to 1.15 grams/cc. The oil that is recovered at this stage in the process has a much more desirable quality in terms of color and free fatty acid content (from about 2% to about 5%) as compared to oil that is recovered downstream, particularly oil recovered after saccharification and fermentation. In particular, the color of the pre-saccharification recovered oil is lighter in color and lower in free fatty acid content. The oil yield can include 0.2 lb/bu or greater. In one example, the oil yield is from about 0.1 to about 1.0 lb/bu.

The separated solids portion from the solid/liquid separation step 312 and a portion of the liquefied starch solution from the oil/liquefied starch solution separation step 314 can meet up with the solids from the microfiltration (or similar filtration) step 318, as described below, and be subjected to a further biochemical conversion processing step 320. In an embodiment, about 5% to about 95% of the liquefied starch solution may be sent to the further processing step 320. When the oil/liquefied starch solution separation step 314 is a three phase separation step, the solids portion is also sent to the further processing step 320. Optionally, a portion of the solids portion from the oil/liquefied starch solution separation step 314 may be sent to the microfiltration step 318. In an embodiment, the further processing step 320 is a fermentation step where the sugars are converted, e.g., via a fermenter, to alcohol, such as ethanol or butanol or any other fermentation conversion process or similar sugar utilization/conversion process, followed by distillation and/or separation of the desired component(s) (not shown), which can recover the alcohol or byproduct(s)/compound(s) produced, as is described above with respect to the system and method 200. Following distillation or desired separation step(s), the system and method 300 can include any back end type process(es), which may be known or unknown in the art to process, for example, the whole stillage. The fermentation step may be part of an alcohol production system that receives a sugar stream that is not as desirable or clean, i.e., "dirtier," than the sugar stream being sent and subjected to the same fermentation step as the dirty sugar stream. Other options for the solids stream, aside from fermentation, can include further processing or refining of the solids into feed, microbe based fermentation (as opposed to yeast based) and other various chemical, pharmaceutical or nutraceutical processing (such as propanol, isobutanol, citric acid or succinic acid), and the like. Such processing can occur via a reactor, including, for example, a catalytic or chemical reactor. In one example, the reactor is a fermenter.

The remainder of the liquefied starch solution from the oil/liquefied starch solution separation step 314 next can be sent to the saccharification step 316 whereat complex carbohydrate and oligosaccharides are further broken down into simple sugars, particularly single glucose sugar molecules (i.e., dextrose) to produce a liquefied mash. In particular, at the saccharification step 316, the slurry stream may be subjected to a two-step cook process. The first part of the cook process, in one example, includes adjusting the pH to about 3.5 to about 7.0, with the temperature being maintained between about 30° C. to about 100° C. for 1 to 6 hours to further convert the insoluble starch in the slurry to soluble starch, particularly dextrose. In another example, the pH can be 5.2 to 5.8 or 5.5, for example. In another example, the temperature can be maintained at 80° C. for about 5 hours. Also, an enzyme, such as alpha-amylase may be added here. In one example, the amount of alpha-amylase may be from about 0.0035 to about 0.004 wt % of the slurry stream. In another example, the amount of alpha-amylase may be from about 0.02 to about 0.1 wt % of the total stream.

The second part of the cook process, in one example, may include adjusting the pH to about 3.5 to about 5.0, with the temperature being maintained between about 30° C. to about 100° C. for about 10 minutes to about 5 hours so as to further convert the insoluble starch in the slurry to soluble starch, particularly dextrose. In another example, the pH can be 4.5. In another example, the temperature can be maintained from about 54° C. (130° F.) to about 74° C. (165° F.) for about 4 hours or up to about 60 hours. An enzyme, such as glucoamylase, also may be added here. In one example, the amount of glucoamylase may be from about 0.01 wt % to about 0.2 wt % of the slurry stream. In another example, the amount of glucoamylase may be from about 0.08 wt % to about 0.14 wt % of the slurry stream. Other enzymes or similar catalytic conversion agents may be added at this step or previous steps that can enhance starch conversion to sugar or yield other benefits, such as fiber or cellulosic sugar release, conversion of proteins to soluble proteins, or the release of oil from the germ.

A saccharified sugar stream having a density of about 1.05 grams/cc to about 1.15 grams/cc can result here. At this point, the saccharified sugar stream may be no less than about 90 DE. In another example, the saccharified sugar stream may be no less than 20, 30, 40, 50, 60, 70, or 80 DE. In this example, the saccharified sugar stream may not be considered desirable or "clean" enough, such as for use in biochemical (e.g., biofuel) production, because the total fermentable content of the stream may be no more than 75% of the total solids content in the stream. In this example, the saccharified sugar stream can have a total solids fraction of about 28% to about 36%, such solids including sugar, starch, fiber, protein, germ, oil, and ash, for example. In yet another example, the total fermentable content of the stream is no more than 30, 40, 50, 60, or 70% of the total solids content in the stream. The remaining solids are fiber, protein, oil, and ash, for example. The stream from the saccharification step 316 contains about 0.1 to about 1.0 lb/bu free oil.

After the saccharification step 316 (but before any potential fermentation or processing of the sugar stream), so as to provide a more desirable sugar stream, the saccharified sugar stream is subjected to a microfiltration step 318, which can include a rotary vacuum filter, micro-filter, membrane filtration, precoat/diatomaceous earth filter, or the like, to produce a more desirable sugar stream, which may be considered a purified or refined sugar stream, by substantial separation of the solids portion, primarily fiber, germ, grit, which can include protein, from the liquid sugar portion, which primarily includes sugar (e.g., dextrose), residual oil, and fine solids. In one example, the filter screen size here may be from about 0.1 micron to about 100 microns. In another example, the filter screen size may be from about 5 microns to about 50 microns. Due to the input of water, the sugar stream may have a total solids fraction of 20-35%. In this example, the sugar stream here may be considered purified or refined enough because the total insoluble (unfermentable) solids fraction of the stream is less than 10%. In another example, the total insoluble (unfermentable) solids fraction of the stream is less than or equal to 7%. In another example, the total insoluble (unfermentable) solids fraction of the stream is less than or equal to 5%. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%.

At this point, the separated sugar stream may be no less than about 90 DE. In another example, the liquefied sugar stream may be no less than 20, 30, 40, 50, 60, 70, or 80 DE. In this example, the sugar stream here may be considered desirable or "clean" enough, such as for use in biochemical production, because the total insoluble (unfermentable) solids fraction of the stream is less than or equal to 10% of the total solids of the stream. In another example, the total insoluble (unfermentable) solids fraction of the stream is less than or equal to 7%. In another example, the total insoluble (unfermentable) solids fraction of the stream is less than or equal to 5%. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%. In this example, the stream sent to microfiltration step 318 may have a total solids fraction of about 27%, or in a range of about 20% to about 35%, such solids including sugar, starch, fiber, protein, and/or germ, for example.

The microfiltration step 318 may be replaced by, or additionally include, ultrafiltration, carbon column color removal, filter press, flotation, adsorption, and/or demineralization technologies (e.g., ion exchange). Resin refining, which includes a combination of carbon filtration and demineralization in one step, can also be utilized for refining the sugars. Additionally, due to a low solids content of the sugar stream here, an optional evaporation step (not shown) may be added hereafter to further concentrate the total solids fraction.

As described above, the heavy or solids (raffinate) components from the microfiltration step 318 can be sent to meet up with the separated solids portion from the solid/liquid separation step 312 and the portion of the liquefied starch solution (and optional solids portion) from the oil/liquefied starch solution separation step 314 and subjected to biochemical conversion process step 320. These heavier components, or underflow, can be more concentrated in total solids at about 28%.

In one example, prior to the biochemical conversion process step 320, the combined streams may be subjected to an optional third grinding/particle size reduction step 322, which may involve use of a disc mill, hammer mill, a pin or impact mill, a roller mill, a grind mill, or the like for further grinding of particles. Prior to subjecting the combined streams to the optional third grinding/particle size reduction step 322, the stream may be subjected to an optional liquid/solid separation step 324 to remove a desired amount of liquids therefrom. The liquid/solid separation step 324 separates the liquid portion of the combined stream, which can include remaining free oil, protein, and fine solids (which do not need grinding), from remaining heavy solids cake, which includes the heavier fiber, grit, and germ, which can include bound oil, protein, and/or starch. The liquid/solid separation step 324 uses dewatering equipment, e.g., a paddle screen, a vibration screen, screen decanter centrifuge or conic screen centrifuge, a pressure screen, a preconcentrator, a filter press, or the like, to accomplish separation of the solids from the liquid portion. The fine solids can be no greater than 200 microns. In another example, the fine solids are no greater than 500 microns, which is generally dependent upon the screen size openings used in the liquid/solid separation device(s).

In one example, the dewatering equipment is a paddle screen, which includes a stationary cylinder screen with a high speed paddle with rake. The number of paddles on the paddle screen can be in the range of 1 paddle per 4 to 8 inches of screen diameter. In another example, the dewatering equipment is a preconcentrator, which includes a stationary cylinder screen with a low speed screw conveyor. The conveyor pitch on the preconcentrator can be about ⅙ to about ½ of the screen diameter. The number of paddles on the paddle screen and the conveyor pitch on the preconcentrator can be modified depending on the amount of solids in the feed. The gap between the paddle screen and paddle can range from about 0.04 to about 0.2 inch. A smaller gap gives a drier cake with higher capacity and purer fiber but loses more fiber to filtrate. A larger gap gives a wetter cake with lower capacity and purer liquid (less insoluble solid). The paddle speed can range from 400 to 1200 RPM. In another example, the paddle speed can range from 800 to 900 RPM. A higher speed provides higher capacity but consumes more power. One suitable type of paddle screen is the FQ-PS32 paddle screen, which is available from Fluid-Quip, Inc. of Springfield, Ohio.

The screen for the dewatering equipment can include a wedge wire type with slot opening, or a round hole, thin plate screen. The round hole screen can help prevent long fine fiber from going through the screen better than the wedge wire slot opening, but the round hole capacity is lower, so more equipment may be required if using round hole screens. The size of the screen openings can range from about 45 microns to about 500 microns. In another example, the screen openings can range from 100 to 300 microns. In yet another example, the screen openings can range from 200 to 250 microns.

The wet cake or dewatered solids portion of the stream at the liquid/solid separation step 324 next may be subjected to the optional third grinding/particle size reduction step 322, as described above. After milling, the solids can be mixed with the liquid from the liquid/solid separation step 324, as shown, to form a solid/liquid stream then subjected to the biochemical conversion process step 320.

Concerning now the sugar stream from the microfiltration step 318, this stream can be sent on to a further processing step, such as a fermentation step where the sugars are converted, e.g., via a fermenter, to alcohol, such as ethanol or butanol or any other fermentation conversion process or similar sugar utilization/conversion process, followed by distillation and/or separation of the desired component(s) (not shown), which can recover the alcohol or byproduct(s)/compound(s) produced, as is known in the art. The sugar stream can allow for recovery of a fermentation agent from the fermentation step. The fermentation agent can be recovered by means known in the art and can be dried as a separate product or, for example, can be sent to a protein separation step or other streams/steps, in the system and method 300, which can allow for capture of the fermentation agent and/or used for further processing. Fermentation agent (such as yeast or bacteria) recycling can occur by use of a clean sugar source. Following distillation or desired separation step(s), the system and method 300 can include any back end type process(es), which may be known or unknown in the art to process, for example, the whole stillage. The fermentation step may be part of an alcohol production system that receives a sugar stream that is not as desirable or clean, i.e., "dirtier," than the sugar stream being sent and subjected to the same fermentation step as the dirty sugar stream. Other options for the sugar stream, aside from fermentation, can include further processing or refining of the glucose to fructose or other simple or even complex carbohydrates, processing into feed, microbe based fermentation (as opposed to yeast based) and other various chemical, pharmaceutical, enzymatic, amino acid, or nutraceutical processing (such as propanol, isobutanol, citric acid or succinic acid), and the like. Such processing can occur via a reactor, including, for example, a catalytic or chemical reactor. In one example, the reactor is a fermenter. It should be noted that those skilled in the art will understand that the microfiltration system can include one or more units and may be situated in series and/or parallel flow.

With reference now to FIG. 6, in this dry grind system and method 400, grains such as corn and/or corn particles, for example, can be subjected to an optional first grinding step 402, which involves use of a hammer mill, roller mill, pin mill, impact mill, flaking mill, or the like, either in series or parallel, to grind the corn and/or corn particles to particle sizes less than about ⁷⁄₆₄ inch or, in another example, less than about ¹⁰⁄₆₄ inch and allow for the release of oil therefrom to define free oil. In one example, the screen size for separating the particles can range from about ²⁴⁄₆₄ inch to about ²⁄₆₄ inch. In another example, the resulting particle sizes are from about 50 microns to about 3 mm. The grinding also helps break up the bonds between the fiber, protein, starch, and germ. In one example, screen size or resulting particle size may have little to no impact on the ability to separate the sugar from the remaining kernel or similar raw material component(s). If the carbohydrate source is pre-ground or initially in particulate form, the optional grind step 402 may be excluded from the system and method 400.

Next, the ground corn flour is mixed with backset liquid at slurry tank 404 to create a slurry. Optionally, fresh water may be added so as to limit the amount of backset needed here. An enzyme(s), such as alpha amylase, optionally can be added to the slurry tank 404 or in a slurry blender (not shown) between the optional first grinding step 402 and the slurry tank 404. The slurry may be heated at the slurry tank 404 from about 66° C. (150° F.) to about 93° C. (200° F.) for about 10 min to about 120 min. The stream from the slurry tank 404 contains about 0.5 lb/bu free oil, about 1.5 lb/bu germ (particle size ranges from about 50 microns to about 3 mm), about 1.8 lb/bu grit (particle size ranges from about 50 microns to about 3 mm), which can include starch, and about 4.25 lb/bu fiber (particle size ranges from about 50 microns to about 3 mm).

The stream from the slurry tank 404 next may be subjected to an optional second grinding/particle size reduction step 406, which may involve use of a disc mill, hammer mill, a pin or impact mill, a roller mill, a grind mill, or the like, to further grind the corn particles to particle sizes less than about 850 microns and allow for additional release of oil and protein/starch complexes therefrom. In another example, the particle sizes are from about 300 microns to about 650 mm. The grinding further helps continue to break up the bonds between the fiber, protein, and starch and facilitates the release of free oil from germ particles. The stream from the second grinding/particle size reduction step 406 contains about 0.1 to about 1.0 lb/bu free oil.

Prior to subjecting the stream from the slurry tank 404 to the optional second grinding/particle size reduction step 406, the slurry may be subjected to an optional liquid/solid separation step 408 to remove a desired amount of liquids therefrom. The liquid/solid separation step 408 separates a generally liquefied solution (about 60% to about 80% by volume), which includes free oil, protein, and fine solids (which do not need grinding), from heavy solids cake (about 20% to about 40% by volume), which includes the heavier fiber, grit, and germ, which can include bound oil, protein, and/or starch. The liquid/solid separation step 408 uses dewatering equipment, e.g., a paddle screen, a vibration screen, screen decanter centrifuge or conic screen centrifuge, a pressure screen, a preconcentrator, a filter press, or the like, to accomplish separation of the solids from the liquid portion. The fine solids can be no greater than 200 microns. In another example, the fine solids are no greater than 500 microns, which is generally dependent upon the screen size openings used in the liquid/solid separation device(s).

In one example, the dewatering equipment is a paddle screen, which includes a stationary cylinder screen with a high speed paddle with rake. The number of paddles on the paddle screen can be in the range of 1 paddle per 4 to 8 inches of screen diameter. In another example, the dewatering equipment is a preconcentrator, which includes a stationary cylinder screen with a low speed screw conveyor. The conveyor pitch on the preconcentrator can be about ⅙ to about ½ of the screen diameter. The number of paddles on the paddle screen and the conveyor pitch on the preconcentrator can be modified depending on the amount of solids in the feed. The gap between the paddle screen and paddle can range from about 0.04 inch to about 0.2 inch. A smaller gap gives a drier cake with higher capacity and purer fiber but loses more fiber to filtrate. A larger gap gives a wetter cake with lower capacity and purer liquid (less insoluble solid). The paddle speed can range from 400 to 1200 RPM. In another example, the paddle speed can range from 800 to 900 RPM. A higher speed provides higher capacity but consumes more power. One suitable type of paddle screen is the FQ-PS32 paddle screen, which is available from Fluid-Quip, Inc. of Springfield, Ohio.

The screen for the dewatering equipment can include a wedge wire type with slot opening, or a round hole, thin plate screen. The round hole screen can help prevent long fine fiber from going through the screen better than the wedge wire slot opening, but the round hole capacity is lower, so more equipment may be required if using round hole screens. The size of the screen openings can range from about 45 microns to about 500 microns. In another example, the screen openings can range from 100 to 300 microns. In yet another example, the screen openings can range from 200 to 250 microns. Smaller screen openings tend to increase the protein/oil/alcohol yield with higher equipment and operation cost, whereas larger screen openings tend to lower protein/oil/alcohol yield with less equipment and operation cost.

Returning now to the optional second grinding/particle size reduction step 406, the wet cake or dewatered solids portion of the stream at the liquid/solid separation step 408 (about 60% to 65% water) next may be subjected to the optional second grinding/particle size reduction step 406, as described above. After milling, the solids can be mixed with the liquefied starch solution from the liquid/solid separation step 408, as shown, to form a heavy slurry then subjected to liquefaction step 410.

In particular, the liquefaction step 410 itself can include multiple steps as discussed above and shown in FIG. 3. In one embodiment, the pH can be adjusted here to about 5.2 to about 5.8 and the temperature maintained between about 50° C. to about 105° C. so as to convert the insoluble starch in the slurry to soluble or liquid starch. Other pH ranges, such as from pH 3.5 to 7.0, may be utilized and an acid treatment system using sulfuric acid, for example, may be used as well for pH control and for conversion of the starches to sugars. The slurry may be further subjected to jet cooking whereat the slurry is fed to a jet cooker, heated to about 120° C., held for about 2 min to about 30 min, then forwarded to a flash tank. The jet cooker creates a sheering force that ruptures the starch granules to aid the enzyme in reacting with the starch inside the granule and for hydrating the starch molecules. In another embodiment, the slurry can be subjected to a secondary slurry tank whereat steam is injected directly to the secondary slurry tank and the slurry is maintained at a temperature from about 80° C. to about 100° C. for about 30 minutes to about one hour. In yet another embodiment, the slurry can be subjected to a secondary slurry tank with no steam. In particular, the slurry is sent to a secondary slurry tank without any steam injection and maintained at a temperature of about 80° C. to about 90° C. for 1 to 2 hours. Thereafter, the liquefied slurry may be forwarded to a holding tank for a total holding time of about 1 hour to about 4 hours at temperatures of about 80° C. to about 90° C. to complete the liquefaction step 410. With respect to the optional liquefaction step 410, pH, temperature, and/or holding time may be adjusted as desired.

The slurry stream after the liquefaction step 410 has about 25% to about 36% dry solids (DS) content with all the components contained in the corn kernels, including starches/sugars, protein, fiber, germ, grit, oil, and salts, for example. There generally are three types of solids in the liquefaction stream: fiber, germ, and grit, which can include starch and protein, with all three solids having about the same particle size distribution. The stream from the liquefaction step 410 contains about 1.0 lb/bu free oil, about 1.5 lb/bu germ particle (size ranges from less about 50 microns to about 1 mm), about 4.50 lb/bu protein (size ranges from about 50 microns to about 1 mm), and about 4.25 lb/bu fiber (particle size ranges from about 50 microns to about 3 mm).

From the liquefaction step 410, the liquefied sugar stream can be sent to saccharification step 412 whereat complex carbohydrate and oligosaccharides are further broken down into simple sugars, particularly single glucose sugar molecules (i.e., dextrose) to produce a liquefied mash. In particular, at the saccharification step 412, the slurry stream may be subjected to an optional two-step cook process. The first part of the cook process, in one example, includes adjusting the pH to about 3.5 to about 7.0, with the temperature being maintained between about 30° C. to about 100° C. for 1 to 6 hours to further convert the insoluble starch in the slurry to soluble starch, particularly dextrose. In another example, the pH can be 5.2 to 5.8 or 5.5, for example. In another example, the temperature can be maintained at 80° C. for about 5 hours. Also, an enzyme, such as alpha-amylase may be added here. In one example, the amount of alpha-amylase may be from about 0.0035 wt % to about 0.04 wt % of the slurry stream. In another example, the amount of alpha-amylase may be from about 0.02 wt % to about 0.1 wt % of the total stream.

The second part of the cook process, in one example, may include adjusting the pH to about 3.5 to about 5.0, with the temperature being maintained between about 30° C. to about 120° C. for about 10 minutes to about 5 hours so as to further convert the insoluble starch in the slurry to soluble starch, particularly dextrose. In another example, the pH can be 4.5. In another example, the temperature can be maintained from about 54° C. (130° F.) to 74° C. (165° F.) for about 4 hours or up to about 60 hours. An enzyme, such as glucoamylase, also may be added here. In one example, the amount of glucoamylase may be from about 0.01 wt % to about 0.2 wt % of the slurry stream. In another example, the amount of glucoamylase may be from about 0.08 wt % to about 0.14 wt % of the slurry stream. Other enzymes or similar catalytic conversion agents may be added at this step or previous steps that can enhance starch conversion to sugar or yield other benefits, such as fiber or cellulosic sugar release, conversion of proteins to soluble proteins, or the release of oil from the germ.

A saccharified sugar stream having a density of about 1.05 grams/cc to about 1.15 grams/cc can result here. At this point, the saccharified sugar stream may be no less than about 90 DE. In another example, the saccharified sugar stream may be no less than 20, 30, 40, 50, 60, 70, or 80 DE. In this example, the saccharified In this example, the saccharified sugar stream can have a total solids fraction of about 25% to about 36%, such solids including sugar, starch, fiber, protein, germ, oil, and ash, for example. In yet another example, the total fermentable content of the stream is no more than 20, 30, 40, 50, 60, 70 or 80% of the total solids content in the stream. The remaining solids are fiber, protein, oil, and ash, for example. The stream from the saccharification step 412 contains about 0.1 lb/bu to about 1.0 lb/bu free oil.

After the saccharification step 412 (but before any fermentation or other processing of the sugar stream), so as to provide a more desirable sugar stream, the saccharified sugar stream can be subjected to a solid/liquid separation step 414 and an oil/saccharified starch solution separation step 416. In particular, the solid/liquid separation step 414 uses any suitable filtration device, e.g., a pre-concentrator, paddle screen, pressure screen, fiber centrifuge, decanter, and the like, to separate the liquid from the solid material. The screen openings can range from about 50 microns to about 500 microns and will be selected to desirably separate the fiber, grit, and germ particles from the liquid, which primarily includes the saccharified starch solution with small amounts of oil, free protein (mainly gluten), and starch. In one example, the screen openings are about 50 microns.

The liquid portion can go to the oil/saccharified starch solution separation step 416 whereat the liquid portion can be subjected to an oil separation device to separate out the oil before sending the saccharified starch solution to the microfiltration (or similar filtration) step 418, which is discussed below. The oil/saccharified starch solution separation step 416 can use any type of oil separation device, such as a mud centrifuge, two or three phase decanter, disc decanter, two or three phase disc centrifuge, flotation tank, dissolved air flotation tank/system, and the like, to separate oil from the sugar stream by taking advantage of density differences. With a three-phase device, such as a three phase centrifuge or decanter, a heavier solids portion optionally can be separated out at the oil/saccharified starch solution step 416 from the oil and saccharified starch solution. At oil/saccharified starch solution separation step 416, the saccharified starch solution is used as heavy media liquid to float the oil, which has a density of about 1.05 grams/cc to about 1.15 grams/cc. The oil that is recovered at this stage in the process has a much more desirable quality in terms of color and free fatty acid content (from about 2% to about 5%) as compared to oil that is recovered downstream, particularly oil recovered after fermentation. In particular, the color of the pre-microfiltration recovered oil is lighter in color and lower in free fatty acid content. The oil yield can include 0.1 lb/bu or greater. In one example, the oil yield is from about 0.1 lb/bu to about 1.0 lb/bu.

The separated solids portion from the solid/liquid separation step 414 can meet up with the solids from the microfiltration (or similar filtration) step 418 and be subjected to a further biochemical conversion processing step 420. When the oil/saccharified starch solution separation step 416 is a three phase separation step, the solids portion is also sent to the further processing step 420. Optionally, a portion of the solids portion from the oil/saccharified starch solution separation step 416 may be sent to the microfiltration step 418. In an embodiment, the further processing step 420 is a fermentation step where the sugars are converted, e.g., via a fermenter, to alcohol, such as ethanol or butanol or any other fermentation conversion process or similar sugar utilization/conversion process, followed by distillation and/or separation of the desired component(s) (not shown), which can recover the alcohol or byproduct(s)/compound(s) produced, as is described above with respect to the system and method 400. Following distillation or desired separation step(s), the system and method 400 can include any back end type process(es), which may be known or unknown in the art to process, for example, the whole stillage. The fermentation step may be part of an alcohol production system that receives a sugar stream that is not as desirable or clean, i.e., "dirtier," than the sugar stream being sent and subjected to the same fermentation step as the dirty sugar stream. Other options for the solids stream, aside from fermentation, can include further processing or refining of the solids into feed, microbe based fermentation (as opposed to yeast based) and other various chemical, pharmaceutical or nutraceutical processing (such as propanol, isobutanol, citric acid or succinic acid), and the like. Such processing can occur via a reactor, which can include a fermenter.

After the oil/saccharified starch solution separation step 416 (but before any potential fermentation or processing of the sugar stream), so as to provide a more desirable sugar stream, the saccharified sugar stream can be subjected to microfiltration step 418, which can include a rotary vacuum filter, micro-filter, membrane filtration, precoat/diatomaceous earth filter a belt filter, or the like, to produce a more desirable sugar stream, which may be considered a purified or refined sugar stream, by substantial separation of the solids portion, primarily fiber, germ, grit, which can include protein, from the liquid sugar portion, which primarily includes sugar (e.g., dextrose), residual oil, and fine solids. In one example, the filter screen size here may be from about 0.1 micron to about 100 microns. In another example, the filter screen size may be from about 5 microns to about 50 microns. Due to the input of water, the sugar stream may have a total solids fraction of 20% to 35%. In this example, the sugar stream here may be considered desirable or "clean" enough, such as for use in biochemical production, because the total insoluble (unfermentable) solids fraction of the stream is less than or equal to 10%. In another example, the total insoluble (unfermentable) solids fraction of the stream is less than or equal to 7%. In another example, the total insoluble (unfermentable) solids fraction of the stream is less than or equal to 5%. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%.

At this point, the separated sugar stream may be no less than about 90 DE. In another example, the separated sugar stream may be no less than 20, 30, 40, 50, 60, 70, or 80 DE. In this example, the sugar stream here may be considered desirable or "clean" enough, such as for use in biochemical production, because the total insoluble (unfermentable) solids fraction of the stream is less than or equal to 10% of the total solids of the stream. In another example, the total insoluble (unfermentable) solids fraction of the stream is less than or equal to 7%. In another example, the total insoluble (unfermentable) solids fraction of the stream is less than or equal to 5%. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%. In this example, the stream sent to microfiltration step 418 may have a total solids fraction of about 23%, with a range of about 20% to about 35%, such solids including sugar, starch, fiber, protein, and/or germ, for example.

The microfiltration step 418 may be replaced by, or additionally include, ultrafiltration, carbon column color removal, filter press, flotation, adsorption, and/or demineralization technologies (e.g., ion exchange). Resin refining, which includes a combination of carbon filtration and demineralization in one step, can also be utilized for refining the sugars. Additionally, due to a low solids content of the sugar stream here, an optional evaporation step (not shown) may be added hereafter to further concentrate the total solids fraction.

As described above, the heavy or solids (raffinate) components from the microfiltration step 418 can be sent to meet up with the separated solids portion from the solid/liquid separation step 414 and the optional solids portion from the oil/saccharified starch solution separation step 416 and subjected to biochemical conversion process step 420. These heavier components, or underflow, can be more concentrated in total solids at about 25% or in a range of about 20% to about 35%.

In one example, prior to the biochemical conversion process step 420, the combined streams may be subjected to an optional third grinding/particle size reduction step 422, which may involve use of a disc mill, hammer mill, a pin or impact mill, a roller mill, a grind mill, or the like for further grinding of particles. Prior to subjecting the combined streams to the optional third grinding/particle size reduction step 422, the stream may be subjected to an optional liquid/solid separation step 424 to remove a desired amount of liquids therefrom. The liquid/solid separation step 424 separates the liquid portion of the combined stream, which can include remaining free oil, protein, and fine solids (which do not need grinding), from remaining heavy solids cake, which includes the heavier fiber, grit, and germ, which can include bound oil, protein, and/or starch. The liquid/solid separation step 424 uses dewatering equipment, e.g., a paddle screen, a vibration screen, screen decanter centrifuge or conic screen centrifuge, a pressure screen, a preconcentrator, a filter press, or the like, to accomplish separation of the solids from the liquid portion. The fine solids can be no greater than 200 microns. In another example, the fine solids are no greater than 500 microns, which is generally dependent upon the screen size openings used in the liquid/solid separation device(s).

In one example, the dewatering equipment is a paddle screen, which includes a stationary cylinder screen with a high speed paddle with rake. The number of paddles on the paddle screen can be in the range of 1 paddle per 4 to 8 inches of screen diameter. In another example, the dewatering equipment is a preconcentrator, which includes a stationary cylinder screen with a low speed screw conveyor. The conveyor pitch on the preconcentrator can be about ⅙ to about ½ of the screen diameter. The number of paddles on the paddle screen and the conveyor pitch on the preconcentrator can be modified depending on the amount of solids in the feed. The gap between the paddle screen and paddle can range from about 0.04 to about 0.2 inch. A smaller gap gives a drier cake with higher capacity and purer fiber but loses more fiber to filtrate. A larger gap gives a wetter cake with lower capacity and purer liquid (less insoluble solid). The paddle speed can range from 400 to 1200 RPM. In another example, the paddle speed can range from 800 to 900 RPM. A higher speed provides higher capacity but consumes more power. One suitable type of paddle screen is the FQ-PS32 paddle screen, which is available from Fluid-Quip, Inc. of Springfield, Ohio.

The screen for the dewatering equipment can include a wedge wire type with slot opening, or a round hole, thin plate screen. The round hole screen can help prevent long fine fiber from going through the screen better than the wedge wire slot opening, but the round hole capacity is lower, so more equipment may be required if using round hole screens. The size of the screen openings can range from about 45 microns to about 500 microns. In another example, the screen openings can range from 100 to 300 microns. In yet another example, the screen openings can range from 200 to 250 microns.

The wet cake or dewatered solids portion of the stream at the liquid/solid separation step 424 next may be subjected to the optional third grinding/particle size reduction step 422, as described above. After milling, the solids can be mixed with the liquid from the liquid/solid separation step 424, as shown, to form a solid/liquid stream then subjected to the biochemical conversion process step 420.

The sugar stream from the microfiltration step 418 can be sent on to a further processing step, such as a fermentation step where the sugars are converted, e.g., via a fermenter, to alcohol, such as ethanol or butanol or any other fermentation conversion process or similar sugar utilization/conversion process, followed by distillation and/or separation of the desired component(s) (not shown), which can recover the alcohol or byproduct(s)/compound(s) produced, as is known in the art. The sugar stream can allow for recovery of a fermentation agent from the fermentation step. The fermentation agent can be recovered by means known in the art and can be dried as a separate product or, for example, can be sent to a protein separation step or other streams/steps, in the system and method 400, which can allow for capture of the fermentation agent and/or used for further processing. Fermentation agent (such as yeast or bacteria) recycling can occur by use of a clean sugar source. Following distillation or desired separation step(s), the system and method 400 can include any back end type process(es), which may be known or unknown in the art to process, for example, the whole stillage. The fermentation step may be part of an alcohol production system that receives a sugar stream that is not as desirable or clean, i.e., "dirtier," than the sugar stream being sent and subjected to the same fermentation step as the dirty sugar stream. Other options for the sugar stream, aside from fermentation, can include further processing or refining of the glucose to fructose or other simple or even complex carbohydrates, processing into feed, microbe based fermentation (as opposed to yeast based) and other various chemical, pharmaceutical, enzymes, amino acids or nutraceutical processing (such as propanol, isobutanol, citric acid or succinic acid), and the like. Such processing can occur via a reactor, which can include a fermenter. It should be noted that those skilled in the art will understand that the microfiltration system can include one or more units and may be situated in series and/or parallel flow.

Also, further modifications can be made to the above systems and methods 200, 300, 400 to improve co-product recovery, such as oil recovery using surfactants and other emulsion-disrupting agents. In one example, emulsion-disrupting agents, such as surfactants, or flocculants may be added prior to steps in which emulsions are expected to form or after an emulsion forms in the method. For example, emulsions can form during centrifugation such that incorporation of surfactants prior to or during centrifugation can improve oil separation and recovery. In one example, the syrup stream pre-oil separation can also have emulsion breakers, surfactants, and/or flocculants added to the evaporation system to aid in enhancing the oil yield. This may result in an additional 0.05 to 0.5 lb/bu oil yield gain.

While the present invention has been illustrated by a description of various embodiments and while these embodiments have been described in considerable detail, it is not the intention of the applicant to restrict or in any way limit the scope of the appended claims to such detail. For example, various enzymes (and types thereof) such as amylase, alpha-amylase, glucoamylase, fungal, cellulase, cellobiose, protease, phytase, and the like can be optionally added, for example, before, during, and/or after any number of steps in the systems and methods 200, 300, 400 including the slurry tank 204, 304, 404 the second grinding step 306, 406 the liquefaction step 208, 310, 410 and/or the saccharification step 214, 316, 412 such as to enhance the separation of components, such as to help break the bonds between protein, starch, and fiber and/or to help convert starches to sugars and/or help to release free oil. In addition, temperature, pH, surfactant, and/or flocculant adjustments may be adjusted, as needed or desired, at the various steps throughout the systems and methods 200, 300, 400 including at the slurry tank 204, 304, 404, etc., such as to optimize the use of enzymes or chemistries. Additional advantages and modifications will readily appear to those skilled in the art. Thus, the invention in its broader aspects is therefore not limited to the specific details, representative apparatus and method and illustrative example shown and described. Accordingly, departures may be made from such details without departing from the spirit or scope of applicant's general inventive concept.

What is claimed is:

1. A method for producing a sugar stream with front end oil separation comprising:
   mixing ground grain particles with a liquid to produce a slurry including starch and free oil;
   subjecting the slurry to liquefaction to provide a liquefied starch solution including the free oil followed by separating the free oil from the liquefied starch solution to produce only two streams with one stream including the separated free oil and the other stream including the liquified starch solution, wherein the separating of the free oil occurs prior to saccharification of the starch to yield an oil by product;
   thereafter, subjecting at least a portion of the liquefied starch solution to saccharification to convert the starch to simple sugars and produce a saccharified stream including the simple sugars;
   after saccharification but prior to further processing of the simple sugars, initially separating the saccharified stream, via microfiltration, into a first solids portion and a first liquid portion including the simple sugars, wherein the first liquid portion is a sugar stream having a dextrose equivalent of at least 20 DE and a total unfermentable solids fraction that is less than or equal to 30% of a total solids content; and
   subjecting the first solids portion to fermentation followed by distillation thereby producing ethanol and separately subjecting the sugar stream to at least one of carbon filtration, ion exchange, or evaporation followed by a sugar conversion process to produce a biochemical other than ethanol, which remains separate from the ethanol produced from the first solids portion.

2. The method of claim 1 further comprising, after mixing the ground grain particles with the liquid to produce the slurry and prior to subjecting the slurry to liquefaction, subjecting the slurry to grinding.

3. The method of claim 2 further comprising, after mixing the grain particles with the liquid to produce the slurry and prior to subjecting the slurry to the grinding, separating the slurry into a solids portion and a liquid portion including the starch and free oil, and wherein subjecting the slurry to the grinding comprises subjecting the solids portion to the grinding to produce a ground solids portion, and further comprising rejoining the separated liquid portion from the slurry with the ground solids portion prior to subjecting the slurry to liquefaction.

4. The method of claim 1 wherein the first liquid portion includes the simple sugars and additional solids, the method further comprising, after separating the saccharified stream into the first solids portion and the first liquid portion, separating, via a membrane, the first liquid portion into a second solids portion including the additional solids and a second liquid portion including the simple sugars, wherein the second liquid portion comprises refined sugar.

5. The method of claim 4 further comprising rejoining the second solids portion with the first solids portion and subjecting the rejoined solids portion to fermentation followed by distillation.

6. The method of claim 1 wherein the sugar conversion process is fermentation.

7. The method of claim 1 wherein the sugar conversion process includes a catalytic or chemical reaction.

8. The method of claim 1 wherein the yield of the oil by-product is greater than 0.05 lb/bu.

9. The method of claim 1 wherein separately subjecting the sugar stream to at least one of carbon filtration, ion exchange, or evaporation comprises subjecting the sugar stream to carbon filtration, followed by ion exchange, followed by evaporation, and then followed by the sugar conversion process to produce a biochemical other than ethanol.

10. A method for producing a sugar stream with front end oil separation comprising:
    mixing ground grain particles with a liquid to produce a slurry including starch and free oil;
    subjecting the slurry to liquefaction to provide a liquefied starch solution including the free oil followed by separating a solids portion including fiber and germ from the liquefied starch solution and then separating the free oil from the liquefied starch solution to produce only two streams with one stream including the separated free oil and the other stream including the liquified starch solution, wherein the separating of the free oil occurs prior to saccharification of the starch to yield an oil by product;
    thereafter, subjecting at least a portion of the liquefied starch solution to saccharification to convert the starch to simple sugars and produce a saccharified stream including the simple sugars;
    after saccharification but prior to further processing of the simple sugars, initially separating the saccharified stream, via microfiltration, into a first solids portion and a first liquid portion including the simple sugars, wherein the first liquid portion is a sugar stream having a dextrose equivalent of at least 20 DE and a total unfermentable solids fraction that is less than or equal to 30% of a total solids content; and subjecting the first solids portion to fermentation followed by distillation thereby producing ethanol and separately subjecting the sugar stream to at least one of carbon filtration, ion exchange, or evaporation followed by a sugar conversion process to produce a biochemical other than ethanol, which remains separate from the ethanol produced from the first solids portion.

11. The method of claim 10 further comprising, after separating the free oil from the liquefied starch solution, rejoining and subjecting the separated solids portion and the liquefied starch solution to saccharification.

12. The method of claim 10 further comprising combining the separated solids portion from the liquefied starch solution and the first solids portion and subjecting the combined solids portions to fermentation followed by distillation thereby producing ethanol.

13. The method of claim 12 further comprising, after combining the separated solids portion from the liquefied starch solution and the first solids portion, separating the combined solids portions into a third solids portion and a third liquid portion, subjecting the third solids portion to grinding, and rejoining the separated third liquid portion with the ground third solids portion then subjecting the combination to fermentation followed by distillation thereby producing ethanol.

14. The method of claim 10 wherein separately subjecting the sugar stream to at least one of carbon filtration, ion exchange, or evaporation comprises separately subjecting the sugar stream to carbon filtration, followed by ion exchange, followed by evaporation, and then followed by the sugar conversion process to produce a biochemical other than ethanol.

15. A method for producing a sugar stream with front end oil separation comprising:

mixing ground grain particles with a liquid to produce a slurry including starch and free oil;

subjecting the slurry to liquefaction to provide a liquefied starch solution including the free oil followed by separating the free oil from the liquefied starch solution to produce only two streams with one stream including the separated free oil and the other stream including the liquified starch solution, wherein the separating of the free oil occurs prior to saccharification of the starch to yield an oil by product;

thereafter, subjecting at least a portion of the liquefied starch solution to saccharification to convert the starch to simple sugars and produce a saccharified stream including the simple sugars;

after saccharification but prior to further processing of the simple sugars, initially separating the saccharified stream into a first solids portion and a first liquid portion including the simple sugars, wherein the first liquid portion is a sugar stream having a dextrose equivalent of at least 20 DE and a total unfermentable solids fraction that is less than or equal to 30% of a total solids content; and subjecting the first solids portion to fermentation followed by distillation thereby producing ethanol and separately subjecting the sugar stream to at least one of carbon filtration, ion exchange, or evaporation followed by a sugar conversion process to produce a biochemical other than ethanol, which remains separate from the ethanol produced from the first solids portion.

16. The method of claim 15 wherein after saccharification but prior to further processing of the simple sugars, initially separating the saccharified stream, via filtration, into a first solids portion and a first liquid portion including the simple sugars.

* * * * *